(12) United States Patent
Arendt et al.

(10) Patent No.: US 9,452,415 B2
(45) Date of Patent: Sep. 27, 2016

(54) SORBENT COMPRISING ON ITS SURFACE A CATIONIC OR PROTONIZABLE ALIPHATIC RESIDUE FOR THE PURIFICATION OF ORGANIC MOLECULES

(71) Applicant: INSTRACTION GMBH, Mannheim (DE)

(72) Inventors: Markus Arendt, Hockenheim (DE); Björn Degel, Hassloch (DE); Thomas Schwarz, Leichlingen (DE); Gerhard Stumm, Hamburg (DE); Martin Welter, Heidelberg (DE)

(73) Assignee: INSTRACTION GMBH, Mannheim (DE)

( * ) Notice: Subject to any disclaimer, the term of this patent is extended or adjusted under 35 U.S.C. 154(b) by 411 days.

(21) Appl. No.: 14/344,718

(22) PCT Filed: Sep. 17, 2012

(86) PCT No.: PCT/EP2012/068198
§ 371 (c)(1),
(2) Date: Mar. 13, 2014

(87) PCT Pub. No.: WO2013/037994
PCT Pub. Date: Mar. 21, 2013

(65) Prior Publication Data
US 2015/0005487 A1 Jan. 1, 2015

(30) Foreign Application Priority Data
Sep. 15, 2011 (EP) .................................... 11181412

(51) Int. Cl.
| | | |
|---|---|---|
| *B01J 20/22* | (2006.01) |
| *B01J 20/286* | (2006.01) |
| *B01D 15/38* | (2006.01) |
| *B01J 20/32* | (2006.01) |
| *C07D 313/00* | (2006.01) |
| *C07B 63/00* | (2006.01) |
| *C07D 305/14* | (2006.01) |
| *C07H 3/02* | (2006.01) |
| *C07H 17/08* | (2006.01) |
| *C07D 215/18* | (2006.01) |
| *C07D 493/22* | (2006.01) |
| *C07C 37/82* | (2006.01) |
| *A61K 31/337* | (2006.01) |
| *A61K 31/365* | (2006.01) |
| *A61K 31/47* | (2006.01) |
| *A61K 31/573* | (2006.01) |
| *A61K 31/724* | (2006.01) |
| *C07C 211/09* | (2006.01) |
| *C07C 215/12* | (2006.01) |
| *C07C 225/06* | (2006.01) |
| *C07D 295/185* | (2006.01) |

(52) U.S. Cl.
CPC ............ *B01J 20/286* (2013.01); *A61K 31/337* (2013.01); *A61K 31/365* (2013.01); *A61K 31/47* (2013.01); *A61K 31/573* (2013.01); *A61K 31/724* (2013.01); *B01D 15/3804* (2013.01); *B01J 20/328* (2013.01); *B01J 20/3219* (2013.01); *B01J 20/3248* (2013.01); *B01J 20/3253* (2013.01); *B01J 20/3255* (2013.01); *B01J 20/3285* (2013.01); *C07B 63/00* (2013.01); *C07C 37/82* (2013.01); *C07C 211/09* (2013.01); *C07C 215/12* (2013.01); *C07C 225/06* (2013.01); *C07D 215/18* (2013.01); *C07D 295/185* (2013.01); *C07D 305/14* (2013.01); *C07D 313/00* (2013.01); *C07D 493/22* (2013.01); *C07H 3/02* (2013.01); *C07H 17/08* (2013.01); *B01J 2220/80* (2013.01)

(58) Field of Classification Search
CPC ....................................................... B01J 20/22
USPC .......................................................... 502/401
See application file for complete search history.

(56) References Cited

U.S. PATENT DOCUMENTS

| | | |
|---|---|---|
| 4,381,239 A | 4/1983 | Chibata |
| 5,759,404 A | 6/1998 | Ericsson |
| 2004/0186305 A1 | 9/2004 | Johnson |

FOREIGN PATENT DOCUMENTS

| | | |
|---|---|---|
| EP | 1217012 | 6/2002 |
| WO | WO 91/04086 | 4/1991 |
| WO | WO 01/58561 | 8/2001 |
| WO | WO 2011/012302 | 2/2011 |
| WO | WO 2011/072873 | 6/2011 |

OTHER PUBLICATIONS

International Search Report for PCT/EP2012/068198 of Nov. 26, 2012.

*Primary Examiner* — Edward Johnson
(74) *Attorney, Agent, or Firm* — Hueschen and Sage

(57) ABSTRACT

The present invention relates to a sorbent comprising a solid support material, the surface of which comprises a residue of a general formula (I), wherein the residue is attached via a covalent single bond to a functional group on the surface of either the bulk solid support material itself or of a polymer film on the surface of the solid support material. Furthermore, the present invention relates to the use of the sorbent according to the invention for the purification of organic molecules, in particular pharmaceutically active compounds, preferably in chromatographic application.

15 Claims, 16 Drawing Sheets

Figure 1:
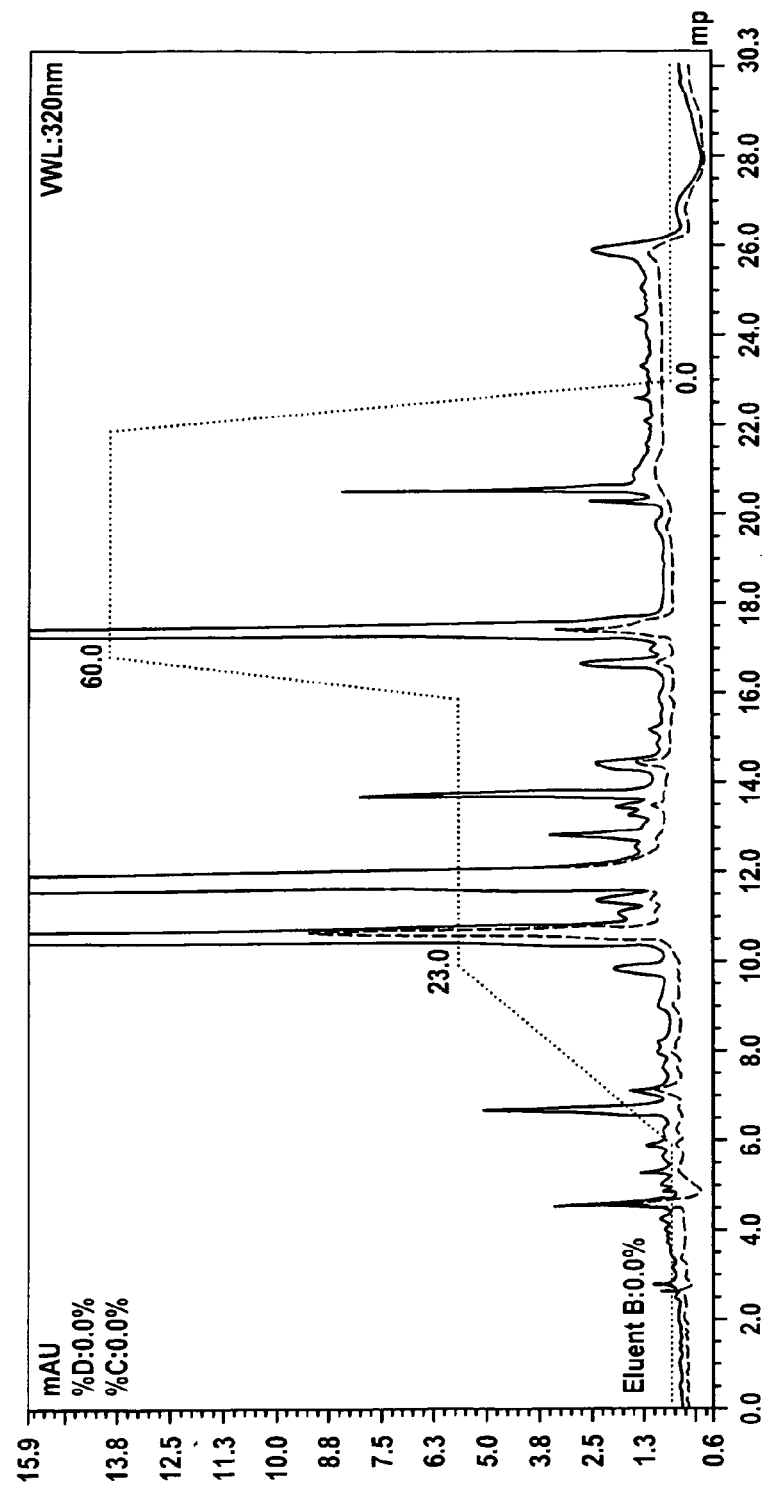

SORBENT COMPRISING ON ITS SURFACE A CATIONIC OR PROTONIZABLE ALIPHATIC RESIDUE FOR THE PURIFICATION OF ORGANIC MOLECULES

The present invention relates to a sorbent comprising a solid support material, the surface of which comprises a residue of a general formula (I), wherein the residue is attached via a covalent single bond to a functional group on the surface of either the bulk solid support material itself or of a polymer film on the surface of the solid support material. Furthermore, the present invention relates to the use of the sorbent according to the invention for the purification of organic molecules, in particular pharmaceutically active compounds, preferably in chromatographic applications.

Chromatography media for organic molecules and biomolecules have traditionally been categorized according to one or more of the following possible modes of interaction with a sample:
  hydrophobic interaction (reversed phase)
  hydrophilic interaction (normal phase)
  cation exchange
  anion exchange
  size exclusion
  metal ion chelation.

The provision of new chemical compounds, either by its discovery in plant extracts or animals or, by chemical synthesis, always demands the provision of new chromatographic materials, the further development of known chromatographic materials or the finding of a new way for the purification of chemical compounds which is simple and cost-effective. That is, there is always a demand for new highly selective downstream purification technologies capable of handling large capacities without up-scaling the required volumes of liquid by the same factor.

Traditional stepwise application of the above chromatographic categories to a given separation problem was accordingly mirrored in a step-by-step, steady improvement of the product purity but also in product losses at every stage which accumulate seriously in the end, not to mention the operational time and cost of goods. Introduction of affinity chromatography at an early stage into the downstream process could be an answer to this demand since the reduction of a consecutive series of sequential chromatography steps into only one could thus be demonstrated many times. Affinity chromatography is sometimes regarded as a class of its own although, from a chemical point of view, it is based on the same interaction modes as above, but usually on a combination of two or more modes. By using affinity chromatography the specific interactions between an analyte and the sorbent may be verified both between the analyte and active residues bound on the surface of a matrix of the chromatographic material and between the analyte and surface characteristics of the matrix itself.

Affinity chromatography has mostly been carried out with bulk gel-phase resins. Pre-eminent gel-forming materials are medium-crosslinked polysaccharides, polyacrylamides, and poly(ethylene oxides). Such hydrogels often ensure a compatible interface which can well accommodate both the active residue of the ligand and the analyte interacting therewith due to their softness (conformational flexibility, elastic modulus), large pore systems, high polarity and high water content, as well as the absence of reactive or denaturing chemical groups. They are able to retain analytes, each as proteins, in their native state, i.e. preserve their correctly folded, three-dimensional structure, state of association, and functional integrity, or do not chemically change the structure of a complex pharmaceutically active compound. The mechanical resistance of these media is, however, much weaker than that of inorganic support materials since they are compressible under an applied pressure and do not tolerate shear stress caused by agitation, column packing or high liquid flow rates. Affinity sorbents that are fully compatible with robust HPLC process conditions are therefore rare.

Only in the recent past it has been recognized that the mechanical resistance of the stationary phase is a bulk property of the sorbent support whereas only a thin layer at the interface between the stationary and the mobile phases is responsible for mass exchange and for the interaction with the biological analyte. Therefore the concept of combining the function of a mechanically very rigid and dimensionality stable, porous 3-dimensional core, and a biocompatible, gel-like interface layer which carries the active residues for binding the analyte has been brought up, and the associated synthetic problems have been technically solved. Such hybrid materials employ loosely crosslinked polymers of high polarity on a base of either an inorganic oxide or a densely crosslinked polymer of low polarity.

It was an object of the present invention to provide a new sorbent for chromatographic applications which allows the simple and cost-effective purification of organic molecules, even when used in chromatographic applications which demand a high stability of the material either with regard to the mechanic stress or in view of the solution characteristics of the eluent.

The present invention therefore provides a sorbent comprising a solid support material, the surface of which comprises a residue of the following general formula (I):

formula (I)

wherein the residue is attached via a covalent single bond represented by the dotted line in formula (I) to a functional group on the surface of either the bulk solid support material itself or of a polymer film on the surface of the solid support material; and wherein the used symbols and indices have the following meanings:

L represents a covalent single bond or is an (h+1)-valent linear aliphatic hydrocarbon group having 1 to 30 carbon atoms or a (h+1)-valent branched or cyclic aliphatic hydrocarbon group having 3 to 30 carbon atoms,
  wherein
  one or more $CH_2$-moieties in said groups may be substituted by a —C(O)—, —C(O)NH—, O, S pr —S(O)$_2$—, and one or more hydrogen atoms may be substituted by D, F, Cl or OH, preferably OH;

$P_B$ represents an organic cationic group or an organic protonizable group;

h is an index representing the number of $P_B$-moieties bound to L and is 1, 2 or 3, more preferred 1 or 2 and most preferred 1,
  with the proviso that, if L represents a covalent single bond, h is 1 and $P_B$ binds to the functional group via a carbon atom of the group $P_B$.

In one embodiment it is further preferred that in the sorbent according to the invention the residues according to formula (I) are attached to the functional group on the surface of the polymer film on the surface of the solid support material.

The group $P_B$ is either an organic cationic group or a protonizable group, i.e. a group which may become a cationic group in solution. Preferably this group is present in cationic form, i.e. protonated form, at a ph in the range of from 6 to 8 in an aqueous solution. Under the term organic group not only groups comprising hydrogen and carbon atoms are to be understood, but also groups comprising nitrogen and hydrogen, such as amines. The presence of the cationic or protonizable group on the surface of the sorbent according to the invention enables the sorbent to enhance its binding capacity with compounds to be purified having a plurality of hydroxyl or chloro groups or having anionic or deprotonizable groups.

It is further preferred that the group $P_B$ is a group comprising at least one nitrogen atom in the form of an amine. The amine may be a primary, secondary, tertiary or quaternary amine. The residues in case of the secondary, tertiary and quaternary amines are preferably $C_{1-6}$-alkyl groups.

The group $P_B$ is more preferred one of the following groups:

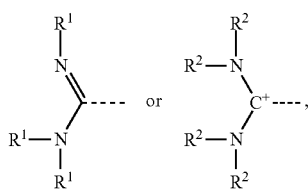

a)

wherein $R^1$ is independently at each occurrence H or $C_{1-6}$-alkyl, preferably H or $CH_3$ and more preferably each $R^1$ has the same meaning, and $R^2$ is independently at each occurrence a $C_{1-6}$-alkyl, preferably $CH_3$ and more preferably each $R^2$ has the same meaning;

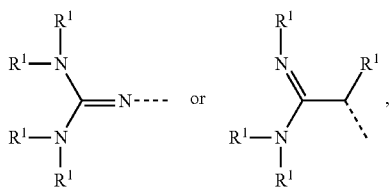

b)

wherein $R^1$ is independently at each occurrence H or $C_{1-6}$-alkyl; and wherein each $R^1$ of the group $N(R^1)_2$ may form together with each $R^1$ of the other groups, independently of each other, a unit $—(CH_2)_p—$, where in p is 2, 3, 4 or 5;

c) $—N(R^3)_2$ or $—[N(R^3)_3]^+$, wherein $R^3$ is H, $C_{1-6}$-alkyl, a mono- or polycyclic aromatic ring system or a mono- or polycyclic heteroaromatic ring system;

d) pyrrolidine, piperidine, morpholine or piperazine, being substituted in position 4 with $R^3$, which has the same meaning as defined under item c), piperazine being more preferred and piperazine wherein $R^3$ is $—CH_3$ or phenyl being most preferred;

e) $—NH—(C_{1-6}$-alkylene)$-NH_2$, wherein $—NH—(CH_2)_n—NH_2$ with n=1, 2, 3, 4, 5 or 6 is more preferred.

It is particularly preferred in the present invention that the group $P_B$ is one of the following groups:

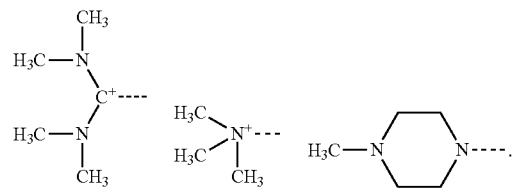

An (h+1)-valent linear aliphatic hydrocarbon group having 1 to 30 carbon atoms or branched or cyclic aliphatic hydrocarbon group having 3 to 30 carbon atoms preferably is one of the following groups: methylene, ethylene, n-propylene, isopropylene, n-butylene, iso-butylene, sec-butylene (1-methylpropylene), tert-butylene, iso-pentylene, n-pentylene, tert-pentylene (1,1-dimethylpropylene), 1,2-dimethylpropylene, 2,2-dimethylpropylene (neopentylene), 1-ethylpropylene, 2-methylbutylene, n-hexylene, iso-hexylene, 1,2-dimethylbutylene, 1-ethyl-1-methylpropylene, 1-ethyl-2-methylpropylene, 1,1,2-trimethylpropylene, 1,2,2-trimethylpropylene, 1-ethylbutylene, 1-methylbutylene, 1,1-dimethylbutylene, 2,2-dimethylbutylene, 1,3-dimethylbutylene, 2,3-dimethylbutylene, 3,3-dimethylbutylene, 2-ethylbutylene, 1-methylpentylene, 2-methylpentylene, 3-methylpentylene, cyclopentylene, cyclohexylene, cycloheptylene, cyclooctylene, 2-ethylhexylene, trifluormethylene, pentafluorethylene, 2,2,2-trifluorethylene, ethenylene, propenylene, butenylene, penteneylene, cyclopentenylene, hexenylene, cyclohexenylene, heptenylene, cycloheptenylene, octenylene of cyclooctenylene, wherein one or more $CH_2$-moieties in said groups may be substituted by a $—C(O)$, $—C(O)NH—$, O, S or $—S(O)_2—$, and one or more hydrogen atoms may be substituted by D, F, Cl or OH, preferably OH.

It is further preferred that—if substituted—only one or two $CH_2$-moieties of L is/are substituted with $—C(O)$, $—C(O)NH—$, O, S or $—S(O)_2$, even more preferred two $CH_2$-moieties are each substituted by $—C(O)—$, which are preferably not in direct neighbourhood to each other. The presence of such heteroatom-containing moieties has the advantage that hydrogen bonds may be formed between these moieties and the compounds to be purified, thereby enhancing the binding strength and the purification capacity.

It is further preferred that—if substituted—only one hydrogen atom of L is substituted by D, F, Cl or OH, preferably OH, since OH is able so form hydrogen bonds.

It is preferred that L is an (h+1)-valent linear aliphatic hydrocarbon group having 1 to 20 carbon atoms, even more preferred 1 to 10 carbon atoms, or a (h+1)-valent branched or cyclic aliphatic hydrocarbon group having 3 to 20 carbon atoms, even store preferred 3 to 10 carbon atoms, wherein one or more $CH_2$-moieties in said groups may be substituted by a $—C(O)$, $—C(O)NH—$, O, S or $—S(O)_2—$, and wherein one or more hydrogen atoms may be substituted by D, F, Cl or OH, preferably OH.

Examples for L as a bivalent linking unit are the following:
a covalent single bond,
$—(C_{1-6}$-alkylene)-,
$—(C_{1-6}$-alkylene)-CH(OH)—$(C_{1-6}$-alkylene)-,
$—(C_{1-6}$-alkylene)-X—$(C_{1-4}$-alkylene)-, wherein X is O, S or $—S(O)_2—$, —(C$_{1-3}$-alkylene)-CH(OH)—(C$_{1-3}$-alkylene)-O—(C$_{1-6}$-alkylene)-O—(C$_{1-3}$-alkylene)-CH(OH)—(C$_{1-3}$-alkylene)-,
—C(O)—,
—C(O)—(C$_{1-6}$-alkylene)-,
—C(O)—(C$_{1-6}$-alkylene)-CH(OH)—(C$_{1-3}$-alkylene)-,
—C(O)—CH(NHC(O)O—(C$_{1-6}$-alkyl))-(C$_{1-6}$-alkylene)-,
—C(O)—(C$_{1-6}$-alkylene)-C(O)—,
—C(O)—(C$_{1-6}$-alkylene)-C(O)—NH—,
—C(O)—(C$_{1-6}$-alkylene)-C(O)—NH—(C$_{1-6}$-alkylene)- and
—C(O)—(C$_{1-6}$-alkylene)-NH—C(O)—(C$_{1-6}$-alkylene)-.

When L is a trivalent linking unit it is preferably of the following formula:

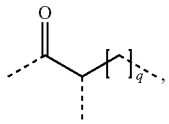

wherein q is 1, 2, 3, 4, 5, 6, 7 or 8.

Preferred examples of L as a bivalent linking unit are the following:
a covalent single bond,
—(CH$_2$)$_2$—,
—(CH$_2$)$_4$—,
—CH$_2$—CH(OH)—CH$_2$—,
—(CH$_2$)$_2$—S(O)$_2$—(CH$_2$)$_2$—,
—CH$_2$CH(OH)—CH$_2$—O—CH$_2$CH$_2$—O—CH$_2$—CH(OH)—CH$_2$—,
—C(O)—CH$_2$—,
—C(O)—CH$_2$CH$_2$CH$_2$—,
—C(O)—CH(CH$_3$)—,
—C(O)—CH$_2$—CH(OH)—CH$_2$—,
—C(O)—CH(NHC(O)O-(iso-butyl))-CH$_2$CH$_2$CH$_2$—,
—C(O)—CH$_2$CH$_2$—C(O)—,
—C(O)—CH$_2$CH$_2$—C(O)—NH—,
—C(O)—CH$_2$CH$_2$—C(O)—NH—CH$_2$CH$_2$— and
—C(O)—CH$_2$CH$_2$CH$_2$—NH—C(O)—(CH(tert-butyl)-.

L is most preferred one of the following units:
a covalent single bond,
—CH$_2$—CH(OH)—CH$_2$—,
—C(O)—CH$_2$—CH(OH)—CH$_2$— (preferably bidding to the support material via the C(O)-group) or
—C(O)—CH$_2$CH$_2$—C(O)—, wherein the dotted lines or free ending lines in all above mentioned definitions or L represent the bonds to the functional group either of the solid support material or of the polymer film and P$_B$, and wherein in all above listed linkers L it is preferred that one first mentioned atom having a free ending line is connected in this position to the solid support material.

According to the present invention a C$_{1-6}$-alkyl is a linear, branched or cyclic alkyl group. Linear alkyl groups have preferably 1 to 6, more preferably 1 to 3 carbon atoms. Branched or cyclic alkyl groups preferably have 3 to 6 carbon atoms. One or more hydrogen atoms of these alkyl groups may be substituted with fluorine atoms. Furthermore, one or more CH$_3$-groups may be substituted with NR, O or S (R is preferably H or C$_{1-6}$-alkyl). If one or more CH$_2$ groups are substituted with NR, O or S, it is preferred that only one of these groups are substituted; even more preferred substituted by an O-atom. Examples of these compounds comprise the following: methyl, ethyl, n-propyl, i-propyl, n-butyl, i-butyl, s-butyl, i-butyl, 2-methylbutyl, n-heptyl, s-pentyl, cyclopentyl, n-hexyl, cyclohexyl, n-heptyl, cycloheptyl, n-octyl, cyclopentyl, 2-ethylhexyl, trifluormethyl, pentafluorethyl and 2,2,2-trifluorethyl.

A C$_{1-6}$-alkylene or C$_{1-3}$-alkylene is an alkyl groups as defined above, wherein one hydrogen atom is not present and the resulting bivalent unit has two bonds.

A mono- or polycyclic aromatic ring system in the sense of the present invention is preferably an aromatic ring system having 6 to 28 carbon atoms as aromatic ring atoms. Under the term "aromatic ring system" a system is to be understood which does not necessarily contain only aromatic groups, but also systems wherein more than one aromatic units may be connected or interrupted by short non-aromatic units (<10% of the atoms different from H, preferably <5% of the atoms different from H), such as sp$^3$-hybridized C, O, N, etc. or —C(O)—. These aromatic ring systems may be mono- or polycyclic, i.e. they may comprise one (e.g. phenyl) or two (e.g. naphthyl) or more (e.g. biphenyl) aromatic rings, which may be condensed or not, or may be a combination of condensed and covalently connected rings. The aromatic atoms of the ring systems may be substituted with D, F, Cl, OH, C$_{1-6}$-alkyl, C$_{1-6}$-alkoxy, NH$_2$, —NO$_2$, —B(OH)$_2$, —CN or —NC.

Preferred aromatic ring systems e.g. are: phenyl, biphenyl, triphenyl, naphthyl, anthracyl, binaphthyl, phenanthryl, dihydrophenanthryl, pyrene, dihydropyrene, chrysene, perylene, tetracene, pentacene, benzpyrene, fluorine, indene and ferrocenyl.

It is further preferred that the mono or polycyclic aromatic ring system has 6 to 14 aromatic ring atoms, which may be substituted or not. That is, it is more preferred that the ring system is phenyl, naphthyl, anthracyl or pyryl, which may be substituted or not.

A mono- or polycystic heteroaromatic ring system in the sense of the present invention is preferably an aromatic ring system having 5 to 28, more preferably 5 to 14, aromatic ring atoms. The heteroaromatic ring system contains at least one heteroatom selected from N, O, S and Se (remaining atoms are carbon). Under the term "heteroaromatic ring system" a system is to be understood which does not necessarily contain only aromatic and/or heteroaromatic groups, but also systems wherein more than one (hetero)aromatic unit may be connected or interrupted by short non-aromatic units (<10% of the atoms different from H, preferably <5% of the atoms different from H), such as sp$^3$-hybridized C, O, N, etc. or —C(O)—. These heteroaromatic ring systems may be mono- or polycyclic, i.e. they may comprise one (e.g. pyridyl) or two or more aromatic rings, which may be condensed or not, or may be a combination of condensed and covalently connected rings.

Preferred heteroaromatic ring systems are for instance 5-membered rings, such as pyrrole, pyrazole, imidazole, 1,2,3-triazole, 1,2,4-triazole, tetrazole, furane, thiophene, selenopheno, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, chinoxalinimidazole, benzoxazole, naphthoxazole, anthroxazole, phenanthroxazole, isoxazole, benzothiazole, benzofurane, isobenzofurane, dibenzofurane, chinoline, isochinoline, pteridine, benzo-5,6-chinoline, benzo-6,7-chinoline, benzo-7,8-chinoline, benzoisochinoline, acridine, phenothiazine, phenoxazine, benzopyridazine, benzopyrimidine, chinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene or combinations of these groups. Even more preferred are imidazole, benzimidazole and pyridine.

The residues according to formula (I) may in a preferred way be all combinations of preferred and most preferred meanings for L and the most preferred meanings of $P_B$.

It is, however, further preferred that the residue of formula (I) is one of the following:

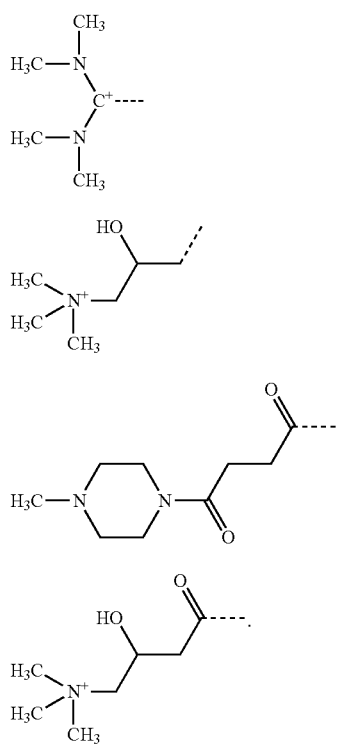

The sorbent according to the invention may further comprise a further residue which is also attached via a covalent single bond to the functional group on the surface of either the bulk solid support material itself or—preferably—of the polymer film on the surface of the solid support material, depending on whether the solid support may comprise a polymer film or not.

The further residue may be any residue being able to interact with the analyte. It is preferred that the further residue is also a residue according to formula (I) which is different from the first residue according to formula (I). In other words, the sorbent according to the invention may comprise at least two residues according to formula (I).

It is, however not in every case necessary that the sorbent of the present invention does comprise more than one kind of residues, i.e. the sorbent of the present invention may in one embodiment not comprise any further residue than the first residue according to formula (I). In this case the residue according to formula (I) is preferably one of the formulae (I)-1, (I)-2, (I)-3 or (I)-4.

In one embodiment the sorbent of the present invention comprises at least two different residues according to formula (I). In this embodiment it is further preferred that the two different residues are selected from the residues of formulae (I)-1, (I)-2, (I)-3 and (I)-4. It is most preferred that the sorbent of the invention comprises a residue according to formula (I)-1 and a residue according to formula (I)-2.

The molar ratio of the residue according to formula (I)-1 to the residue according to formula (I)-2 is preferably in the range of from 5:1 to 35:1, more preferably 15:1 to 30:1 and most preferred 20:1 to 25:1, wherein the amounts of the residues are calculated from elemental analysis.

The solid support material is preferably a macroporous material. The pore size of the solid support material is preferably at least 6 nm, more preferably from 20 to 400 nm and most preferably from 50 to 250 nm. A pore size in this range is important to ensure that the purification capacity is high enough. If the pore size is over the above higher limit the more of the polymer on the surface must be cross-linked leading to a polymer which is not flexible enough. It is believed that than the binding groups may not be able to come into a position which is important to bind the compounds to be purified sufficiently. In case the pore size is too low, the polymer film may cover the pores and the effect of the porosity of the sorbent is lost.

According to an embodiment of the sorbent according to the invention, the solid support material has a specific surface area of from 1 $m^2$/g to 1000 $m^2$/g, more preferred of from 30 $m^2$/g to 800 $m^2$/g and most preferred of from 50 to 500 $m^2$/g.

It is preferred that the solid support material has a porosity of from 30 to 80% by volume, more preferred from 40 to 70% by volume and most preferred from 50 to 60% by volume. The porosity can be determined by mercury intrusion according to DIN 66133. The pore size of the solid support material can also be determined by pore filling with the mercury intrusion method according to DIN 66133. The specific surface area can be determined by nitrogen adsorption with the BET-method according to DIN 66132.

The solid support material may be an organic polymeric material or an inorganic material.

In case the solid support material is a polymeric material, it is substantially non-swellable. For that reason, it is mostly preferred that the polymeric material has a high crosslinking degree.

The polymeric material is preferably crosslinked at a degree of at least 5%, more preferably at least 10% and most preferably at least 15%, based on the total number of crosslinkable groups in the polymeric material. Preferably, the crosslinking degree of the polymeric material does not exceed 50%.

Preferably the polymeric material for the solid support material is selected from the group consisting of generic or surface-modified polystryene, (e.g. poly(styrene-co-dinvinylbenzene)), polystyrene sulfonic acid, polyacrylates, polymethacrylates, polyacrylamides, polyvinylalcohol, polysaccharides (such as starch, cellulose, cellulose esters, amylose, agarose, sepharose, mannan, xanthan and dextran), and mixtures thereof.

The polymeric material possibly used in the present invention preferably has before the crosslinking has been performed 10 to 10000, particularly preferably 10 to 5000 and very particularly preferably 50 to 2000 repeat units. The molecular weight $M_W$ of the polymeric material before the crosslinking has been performed is preferably in the range of 10000 to 2000000 g/mol, particularly preferably in the range of 100000 to 1500000 g/mol, and very particularly preferably in the range of 200000 to 1000000 g/mol. The determination of by $M_W$ can be performed according to standard techniques known to the person skilled in the art by employing gel permeation chromatography (GPC) with polystyrene as internal standard, for instance.

In case the solid support material is an inorganic material, the inorganic material is some kind of inorganic mineral oxide, preferably selected from the group consisting of silica, alumina, magnesia, titania, zirconia, fluorosile, magnetite, zeolites, silicates (cellite, kieselguhr), mica, hydroxyapatite, fluoroapatite, metal-organic frameworks, ceramics and glasses, like controlled pore glass (e.g. trisoperl), metals such as aluminium, silicon, iron, titanium, copper, silver, gold and also graphite or amorphous carbon.

Independent of whether the solid support material is a polymeric material or an inorganic material, the solid support material provides a solid base of minimum rigidity and hardness which functions as an insoluble support and provides a basis for the enlargement of the interface between stationary and mobile phases which is the place of interaction with the analyte as the molecular basis for the process of the partitioning between said phases, and for an increased mechanical strength and abrasiveness, especially under flow and/or pressurized conditions.

The solid support materials according to the invention may be of homogeneous or heterogeneous composition, and therefore also incorporate materials which are compositions of one or more of the materials mentioned above, in particular multi-layered composites.

The solid support material may be a particulate material, preferably having a particle size of from 5 to 500 µm. The solid support material may also be a sheet- or fibre-like material such as a membrane. The external surface of the solid support material thus may be flat (plates, sheets, foils, disks, slides, filters, membranes, woven or nonwoven fabrics, paper) or curved (either concave or convex: spheres, beads, grains, (hollow) fibres, tubes, capillaries, vials, wells in a sample tray).

The pore structure of the internal surface of the solid support material may, inner alia, consist of regular, continuous capillary channels or of cavities of irregular (fractal) geometry. Microscopically, it can be smooth or rough, depending on the way of manufacture. The pore system can either extend continuously throughout the entire solid support material or end in (branched) cavities. The rate of an analyte's interfacial equilibration between its solvation in the mobile phase and its retention on the surface of the stationary phase and thus the efficiency of a continuous flow separation system is largely determined by mass transfer via diffusion through the pores of the solid support material and thus by its characteristic distribution of particle and pore sizes. Pore sizes may optionally show up as asymmetric, multimodal and/or spatially (e.g. cross-sectionally) inhomogeneous distributions.

As mentioned above, the surface of the solid support material is preferably covered with a film of a polymer, which comprises or consists of individual chains. These chains are preferably covalently crosslinked with each other. The polymer is preferably not covalently bound to the surface of the solid support material. The inventors of the present invention have surprisingly found that especially for the purification of compounds having both a hydrophobic and an cationic or protonizable moiety it is important that the polymer is flexible enough to come into a conformation which makes it possible that both the hydrophobic and the cationic or protonizable moieties may come into contact with the hydrophobic and hydrophilic or anionic moieties of the compound to be purified. In case a polymer film would be used which is covalently bound to the surface of the support material the inventors of the present invention observed that the purification capacity significantly decreased. That is, the use of a non-covalently surface bound cross-linked polymer as a polymer film has three advantages: (1) Flexibility of the polymer due to the fact that it is not surface bound; (2) the cross-linking ensures that the film is adhered to the surface of the support material and is not lost; (3) the thickness of the polymer can be adjusted as thin as wanted, if the polymer is not covalently bound to the polymer.

It is further preferred that the polymer covering the support material is a hydrophilic polymer. Hydrophilic properties of the polymer ensure that the hydrophilic interactions between the sorbent and the compound to be purified can take place.

The preferred polymer for the crosslinkable polymer is preferably assembled by at least monomers comprising a hydrophilic group, preferably in its side chain. Preferable hydrophilic groups are $-NH_2$, $-NH-$, $-OH$, $-COOH$, $-OOCCH_3$, anhydrides, $-NHC(O)-$ and saccharides, wherein $-NH_2$ and $-OH$ is more preferred and $-NH_2$ is most preferred.

The polymer film on the surface of the support material preferably comprises functional groups (hydrophilic groups) in a range of from 300 to 700 µmol/mL, more preferably in a range of from 350 to 650 µmol/mL, most preferred in a range of from 400 to 600 µmol/mL, related to the entire volume of the sorbent without residues according to formula (I).

If co-polymers are employed, the preferred co-monomers are simple alkene monomers or polar, inert monomers like vinyl pyrrolidone.

Examples of polymers covering the support material are: polyamines, such as polyvinylamine, polyethylene imine, polyallylamine, polyaminoacids, such as polylysin, etc. as well as functional polymers other than those containing amino groups, such as polyvinyl alcohol, polyvinyl acetate, polyacrylic acid, polymethacrylic acid, their precursor polymers such as poly(maleic anhydride), polyamides, or polysaccharides (cellulose, dextran, pullulan etc.), wherein polyamines such as polyvinylamine and polyallylamine are more preferred and polyvinylamine is most preferred.

Furthermore, the sorbent according to the invention preferably contains residues according to formula (I) in the range of from 50 to 700 µmol/mL, more preferred in the range of from 80 to 650 µmol/mL, most preferred in the range of from 100 to 620 µmol/mL, related to the total volume of the sorbent according to the invention, wherein the amount is determined by elemental analysis.

With respect to a superior purification capacity it is further preferred that in the sorbent according to the invention the molar ratio of the residues according to formula (I) to the amount of functional groups of the polymer (derivatization degree) is preferably more than 0.2, wherein the amount of residues according to formula (I) is determined by elemental analysis and the amount of functional groups is determined by titration of the sorbent before the residues according to formula (I) have been applied.

The polymer can be applied to the macroporous support by all means of coating known to a person skilled in the art such as absorption, vapor phase deposition, polymerization from the liquid, gas or plasma phase, spin coating, surface condensation, wetting, soaking, dipping, rushing, spraying, damping, evaporation, application of electric fields or pressure, as well as methods based on molecular self-assembly such as, for example, liquid crystals, Langmuir Blodgett- or layer-by-layer film formation. The polymer may thereby be coated directly as a monolayer or as multilayer or as a stepwise sequence of individual monolayers on top of each other. It is preferred in the present invention that the polymer is coated to the support material in that the non-cross-linked polymer is given to the support material in an aqueous solution and then cross-linked.

The ratio of the weight of the polymer covering the support material to the weight of the support material preferably ranges from 0.03 to 0.2, more preferably 0.045 to 0.12, in the sorbent according to the invention. If the above ratio is exceeding the upper limit, the polymer film is too thick and the pores of the support material are totally covered/clogged resulting in a sorbent having no available pores. If the above ratio is below the lower limit, the amount of polymer is not enough to cover the entire support material. Furthermore, in the latter case more crosslinking agent would have to be used in order to fix the polymer to the support material, again resulting in a polymer film being not flexible enough.

According to a preferred embodiment of the sorbent according to the invention, the crosslinking degree of the crosslinked polymer is at least 2%, based on the total number of crosslinkable groups in the crosslinked polymer. More preferred the crosslinking degree is of from 5 to 50%, more preferred of from 5 to 30%, most preferred from 10 to 20%, based on the total number of crosslinkable groups in the crosslinked polymer. The crosslinking degree can easily be adjusted by the stoichiometric amount of the crosslinking reagent used. It is assumed that nearly 100 mol % of the crosslinker reacts and forms crosslinks. This can be verified by analytical methods. The crosslinking degree can be determined by MAS-NMR spectroscopy and quantitative determination of the amount of crosslinker in relation to the amount of polymers. This method is most preferred. The crosslinking degree can also be determined by IR spectroscopy based on e.g. C—O—C or OH vibrations using a calibration curve. Both methods are standard analytical methods for a person skilled in the art. If the crosslinking degree is above the upper limit the polymer film is not flexible enough resulting in an inferior purification capacity. Additionally the number and concentration of the available groups for derivatisation are reduced. If the crosslinking degree is below the limit mentioned above the film is not sufficiently stable on the surface of the support material.

The crosslinking reagent used for crosslinking the polymer is preferably selected from the croup consisting of dicarboxylic acids, diamines, diols, urea and bis-epoxides, more preferred dicarboxylic acids and bis-epoxides, such as ethylene glycol diglycidylether, 1,12-bis-(5-norbornen-2,3-dicarboximido)-decandicarboxylic acid, terephthalic acid, biphenyl dicarboxylic acid, ethylene glycol diglycidylether and 1,12-bis-(5-norbornen-2,3-dicarboximido)-decandicarboxylic acid being most preferred. In one embodiment the at least one crosslinking reagent is a linear, conformationally flexible molecule of a length of between 4 and 20 atoms.

Preferred molecular weights of the polymers used range from, but are not limited to, 5000 to 5000 g/mol, which is particularly true for polyvinylamine. Polymers having a molecular weight near the lower limit of the range given above have shown to penetrate even narrow pores of the carrier so that solid state materials with high surface areas and consequently with good mass transfer kinetics, resolution and binding capacity can be used in the sorbents of the present invention.

According to a further embodiment the crosslinked polymer carries functional groups, i.e. the hydrophilic side chain groups mentioned above.

The term "functional group" means any simple, distinct chemical moiety belonging to the cross linked polymer on the surface of the solid support material or to the crosslinkable polymer during preparation of a polymer film on the surface of the solid support material. Thereby, the functional group may serve as chemical attachment point or anchor. Functional groups preferably contain at least one weak bond and/or one heteroatom, preferably a group behaving as nucleophil or electrophil.

The preferred functional groups are primary and secondary amino, hydroxyl, and carboxylic acid or ester groups, when taken before the residues of formulae (I) bane been bound to these groups. When the residues are bound to the functional groups the nature of these groups change with respect to the structure of the residues bound.

The invention also relates to a method for preparing a sorbent, preferably the sorbent according to the invention, comprising:
(i) providing a polymer having functional groups;
(ii) adsorbing a film of said polymer onto the surface of a carrier;
(iii) crosslinking a defined portion of said functional groups of the adsorbed polymer with at least one crosslinking reagent;
(iv) derivatising further defined portions of said functional groups of the crosslinked polymer with one or more residues according to the formulae (I).

The polymer to be adsorbed on the surface of the carrier is preferably solved in an aqueous media wherein the pH is suitably adjusted in order to solve or suspend the polymer. The adsorbing of the polymer on the surface of the carrier is preferably done by dipping the carrier into the solution or suspension containing the polymer. The mixture is then preferably shaked in order to get a complete mix of the ingredients. Capillaric forces make sure that pores of the carrier are soaked with the solution or suspension. Then, the water is preferably evaporated in vacuum at a temperature between 40 and 60° C., thereby depositing the polymer at the walls of the pores in the form of a film. Then, the coated material is preferably suspended in an organic solvent, such as isopropanol or dimethylformamide (DMF), and is preferably crosslinked by means of a crosslinking agent, such as ethylene glycol diglycidyl ether, preferably at a temperature between 25 and 60° C. for 1 to 8 hours.

Depending on the kind of functional groups and depending on the residue according to formula (I) different derivatization strategies of the solid support can be used. If the solid support material contains amino groups as functional groups, residues containing a carboxylic acid group can be attached to the amine nitrogen atom via the carboxylic carbon atom via peptide chemistry using coupling reagents like 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), benzotriazole-1-yl-oxy-tris-pyrrolidino-phosphonium hexafluorophosphate (PyBOP), propylphosphonic anhydride (T3P) etc. or by using reactive groups in the reagent like isocyanates, epoxides or anhydrides. If the solid support material contains amino groups, aliphatic carbon atoms of the residue according to formula (I) may be bound to the amine nitrogen atom via a nucleophilic aliphatic substitution.

If the solid support material contains hydroxy groups, residues according to formula containing a carboxylic acid group before being attached to the functional group may be attached to the oxygen atom of the hydroxy group via the carboxylic carbon atom by using the carboxylic acid chloride or the ester of the carboxylic acid group. If the solid support material contains hydroxy groups, aliphatic carbon atoms of the residue according to formula (I) may be bound to the oxygen atom of the hydroxy group via a nucleophilic aliphatic substitution.

If the solid support material contains carboxylic acid groups, carboxylic acid esters or carboxylic acid anhydrides, the residue according to formula (I) may be attached via nucleophilic attack of a nucleophilic group, such as $-NH_2$, $-OH$, $-SH$ at the electrophilic carbon atom of the carboxylic acid group, acid ester or anhydride, thereby forming an amide, ester or thioester.

In one embodiment of the sorbent according to the invention it is preferred that L is bound to the functional groups which are amine groups, preferably $-NH_2$. Furthermore, it is preferred that the derivatization degree is under 100%, preferably under 90% ensuring that the polymer film comprises free amino groups which may be also be protonized thereby forming an cation providing an sorbent able to form additional ionic bonds to the compounds to be purified. Moreover residues according to formula (I) with the group $P_B$ ensures that the sorbent according to the invention has more flexible cationic or protonizable groups compared to the relatively unflexible amine groups on the surface of the polymer film. All these interactions together are preferred in order ensure a sufficient purification capacity of the sorbent according to the invention.

The sorbent of the present invention may be used for the purification of organic molecules (organic compounds) or the purification of solutions from certain organic molecules. That is, the present invention further refers to the use of a sorbent according to the invention for the purification of organic molecules or the purification of solutions from organic molecules.

The term "purification" is referred to as comprising separating, or increasing the concentration and/or purity of an organic molecule from a mixture containing said organic molecule.

In other words the present invention is also directed to a method of purification of organic molecules which also includes the separation of unwanted organic molecules from a solution by using the sorbent of the present invention.

The use of the sorbent according to the invention for the purification of organic molecules or the method for the purification of organic molecules by using the sorbent according to the invention comprises the following steps:
(i) applying a crude mixture comprising the organic molecules being dissolved or suspended in a liquid on a chromatographic column containing the sorbent according to the invention or a sorbent prepared according to a method of the invention;
(ii) elution of the organic molecule from the column by using an eluent.

The eluent used in step (ii) may be the same solvent as used for the liquid in step (i), but tray also be different, depending on the conditions necessary for the purification of the organic molecules. As liquid in step (i) or eluent in step (ii) every kind of solvent or buffering system applicable in the field of chromatography may be used. Examples of the liquids/solvents used in the present inventions are: tetrahydrofurane, methanol, ethanol, water, glacial acetic acid, acetyl acetate, aqueous formic acid, hexane, heptane, pentane, ethyl acetate, acetic acid, toluene, dichloromethane, trichloromethane, and mixtures of two or more of these solvents. More preferred examples are: tetrahydrofurane, methanol, water, glacial acetic acid, acetyl acetate, aqueous formic acid, hexane, ethyl acetate, acetic acid, toluene, dichloromethane and mixtures of two or more of these solvents. Preferred mixtures of these solvents are the following: tetrahydrofurane/methanol, water/glacial acetic acid, methanol/acetyl acetate, methanol/aqueous formic acid, hexane/ethyl acetate/methanol, water/acetic acid, toluene/methanol, dichloromethane/ethyl acetate and dichloromethane/acetic acid/methanol.

The organic molecules purified by means of the sorbent of the present invention are preferably pharmaceutically active compounds.

The organic molecules to be purified are preferably compounds having either one or more, preferably more, anionic or polar, hydrogen bridging or deprotonizable groups, or are compounds having a plurality of hydroxyl groups or chloro groups. Molecules having one or more of these groups in its structure are able to interact in a preferable way with the cationic or deprotonizable groups of the residue according to formula (I) and/or of the functional groups of the polymer.

The organic molecules have preferably a molecular weight in the range of from 100 to 200000 g/mol, more preferably in the range of from 100 to 150000 g/mol, and most preferred of from 100 to 2500 g/mol.

Particularly preferred as organic molecules used in the use/process of the present invention are paclitaxel, 10-D-acetyl-baccatin III, montelukast, docetaxel, sugammadex, pentamycine and fluocortolone, or derivatives of these molecules, or a mixture of isomers of dichlorophenols, or sugars, preferably mono-sacharides, such as fructose and glucose, most preferably molecules of the following structures:

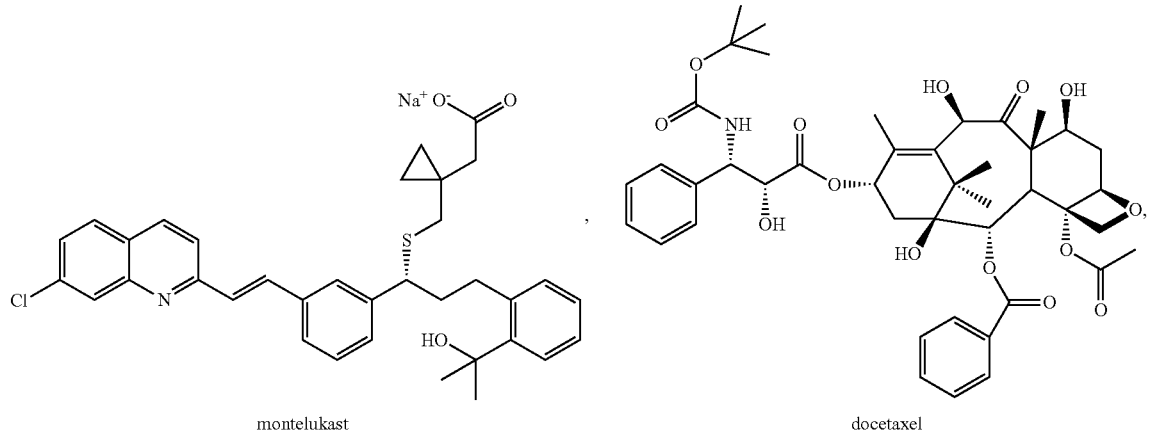

montelukast docetaxel

-continued

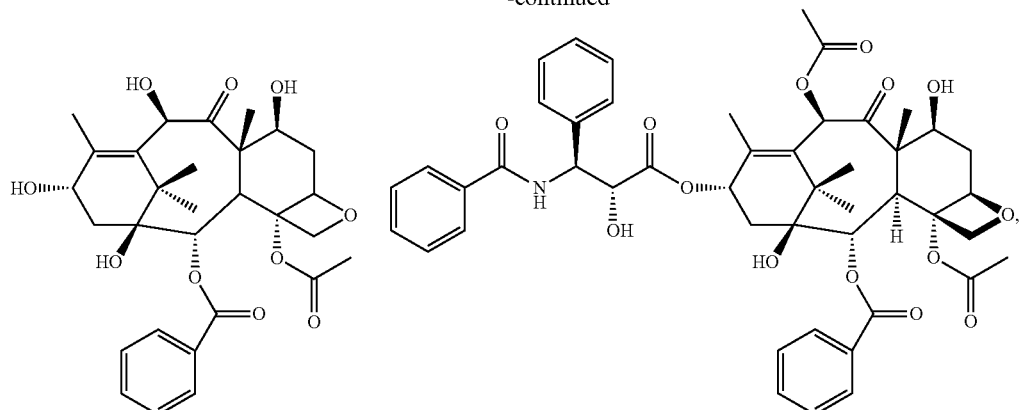

10-D-acetyl-baccatin III paclitaxel

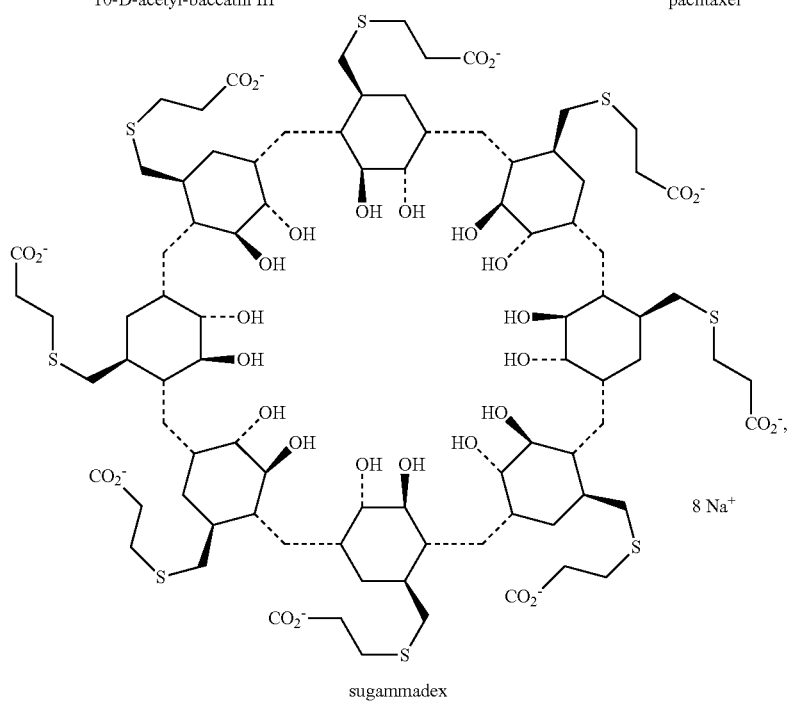

sugammadex

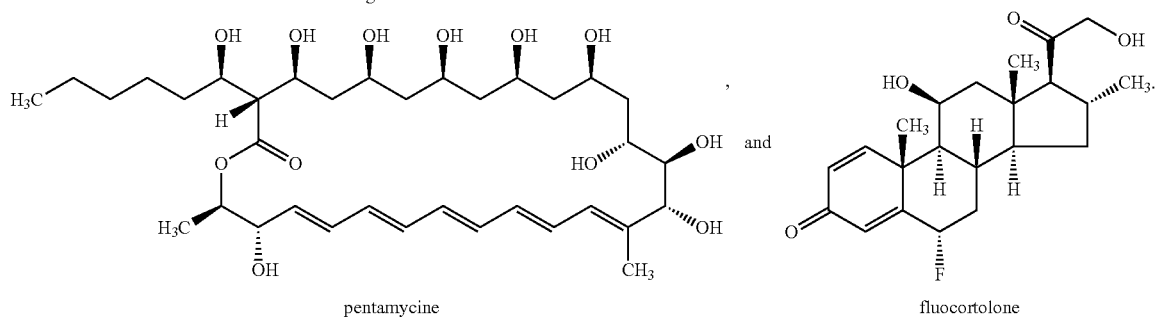

pentamycine fluocortolone

Furthermore, the sorbent according to the invention may also be used for separating endotoxines from solutions. The term "endotoxines" as used in the present invention refers to a class of biochemical substances. Endotoxines are decomposition products of bacteria, which may initiate variable physiologic reactions in humans. Endotoxines are components of the outer cell membrane (OM) of gram-negative bacteria or blue-green algae. From the chemical view endotoxines are lipopolysaccharides (LPS) which are composed of a hydrophilic polysaccharide component and a lipophilic lipide component. In contrast to the bacteria endotoxines atom from, endotoxines are very thermally stable and endure sterilisation. The currently most sensitive method of measuring endotoxines is made by means of the activation of the coagulation cascade in the lysate of amoebocytes which have been isolated from limulus polyphemus. This test is commonly known as the so-called LAL-test.

In the case of the purification of paclitaxel, 10-D-acetyl-baccatin III, montelukast, docetaxel, sugammadex, pentamycine and fluocortolone, or their derivatives, or sugars it is preferred that a sorbent according to the invention is used which comprises a residue according to formula (I).

In the case of the purification of paclitaxel, 10-D-acetyl-baccatin III, montelukast, docetaxel, sugammadex or pentamycine, or their derivatives it is preferred that a sorbent according to the invention is used which comprises only one kind of residues according to formula (I). In this case it is particularly preferred that the residue is one of formulae (I)-1, (I)-2 or (I)-3.

In the case of the purification of 10-D-acetyl-baccatin III, montelukast and docetaxel, or their derivatives, it is preferred that the sorbent according to the invention comprises the residue according to formula (I)-3.

In the case of the purification of paclitaxel, or its derivatives, it is preferred that the sorbent according to the invention comprises either a residue according to formula (I)-2 or to formula (I)-3.

In the case of the purification of sugammadex, or its derivatives, it is preferred that the sorbent according to the invention comprises the residue according to formula (I)-2.

In the case of the purification of pentamycin, or its derivatives, it is preferred that the sorbent according to the invention comprises the residue according to formula (I)-1.

In the case of the purification of fluocortolone, or its derivatives, it is preferred that a sorbent according to the invention is used which comprises two different kinds of residues according so formula (I). It is further preferred that one residue according to formula (I) is that of formula (I)-1 and that one residue according to formula (I) is that of formula (I)-2.

In the case of the separation of a mixture of dichlorophenols or in case of the separation of sugars it is preferred that the sorbent according to the invention is used which comprises the residue according to formula (I)-4.

The invention also relates to a column for liquid chromatography or solid phase extraction comprising a sorbent according to the invention or a sorbent prepared according to a method according to the invention as a stationary phase within a tubular containment and optionally further components such as frits, filter prates, flow distributors, seals, fittings, screwings, valves, or other fluid handling or connection elements. In one embodiment, the method is further characterised by its physical and chemical resistance against applied pressures up to 20 bar, against applied heat up to 110° C., as well as against common sanitisation protocols, thus enabling its repetitive use of up to 1,000 times, preferably up to 5,000 times. The invention also relates to a collection of a plurality of the same or different sorbents according to the invention or of sorbents prepared according to a method according to the invention or of columns according to the invention in the format of a microplate or microchip array, or a multi-capillary or microfluidic device, capable of being processed in parallel.

The invention also relates to a diagnostic or laboratory purification kit comprising a sorbent according to the invention or a sorbent prepared according to a method according to the invention or a column according to the invention or a collection of sorbents or columns according to the invention and, within the same packaging unit, further chemical or biological reagents and/or disposables necessary for carrying out the method according to the invention or a different analytical, diagnostic, or laboratory method different therefrom.

The present invention further refers to the following embodiments:

(i) A method for the purification of organic molecules by using a sorbent according to the invention.
(ii) The method according to embodiment (i), wherein the organic molecules are pharmaceutically active compounds.
(iii) The method according to embodiment (i) or (ii), wherein the organic molecules have a molecular weight in the range of from 100 to 200000 g/mol.
(iv) The method according to any one of the embodiments (i) to (iii), wherein the organic molecules are selected from the group consisting of paclitaxel, 10-D-acetyl-baccatin III, montelukast, docetaxel, sugammadex, pentamycine, fluocortolone, dichlorophenol, the derivatives thereof, and endotoxins.

The present invention is further explained by means of the following figures and examples which should however not be understood as being limiting for the scope of the present invention:

FIGURES

FIG. 1: Comparison of the analytical chromatograms of the crude pentamycin (continuous line) and the purified pentamycin (dashed line) (Example 7).

Figure 2:
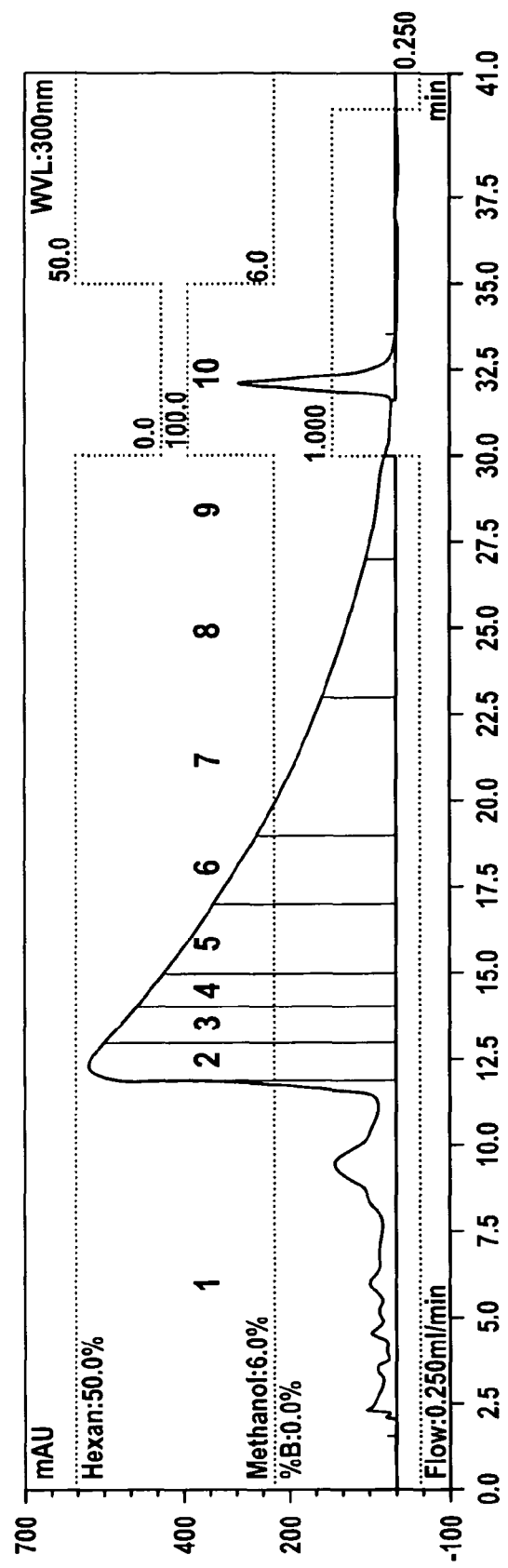

FIG. 2: Fractionation of paclitaxel according to Example 10.

Figure 3:
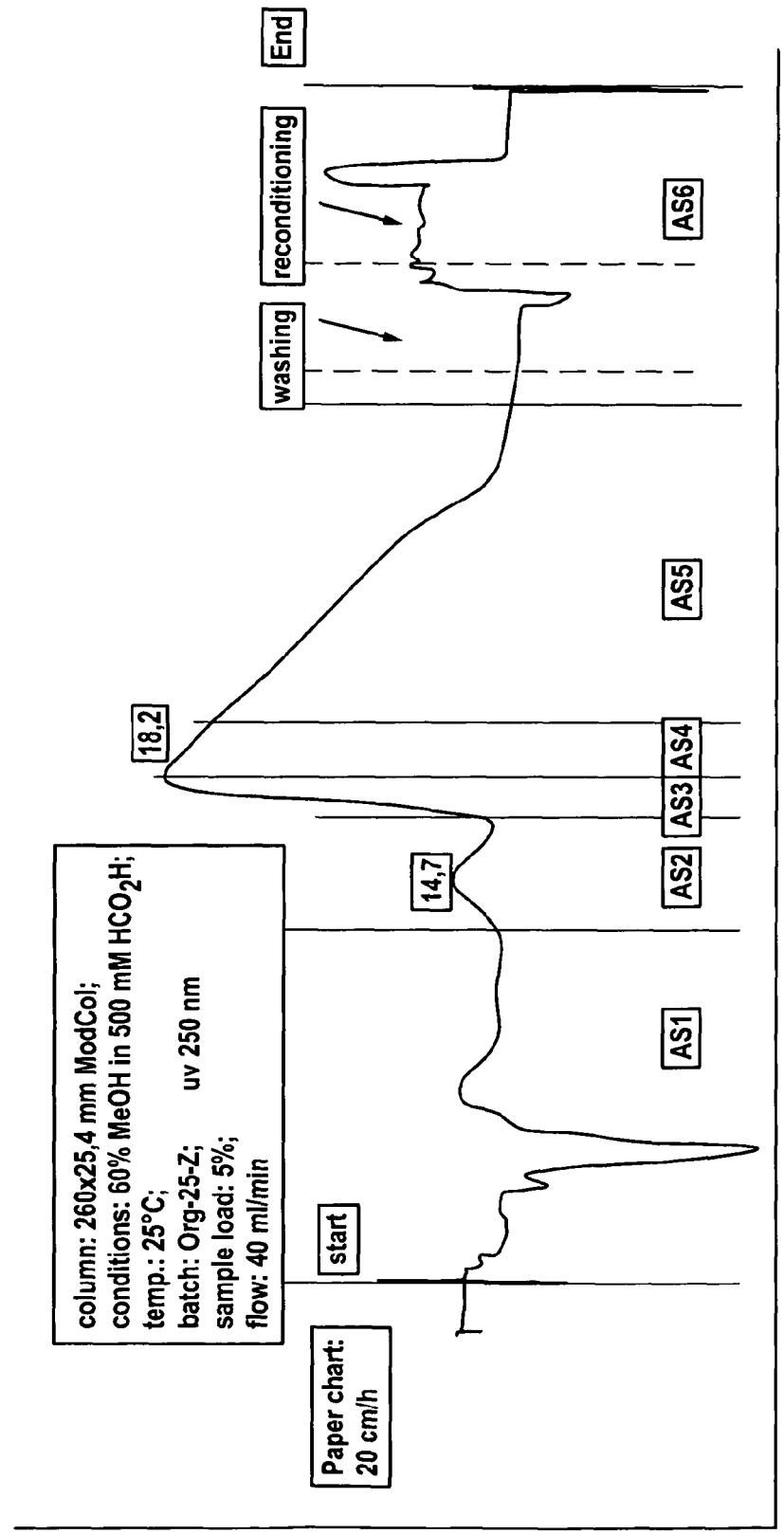

FIG. 3: Printout of the fractionation chromatogram for the purification of sugammadex (Example 9).

Figure 4:
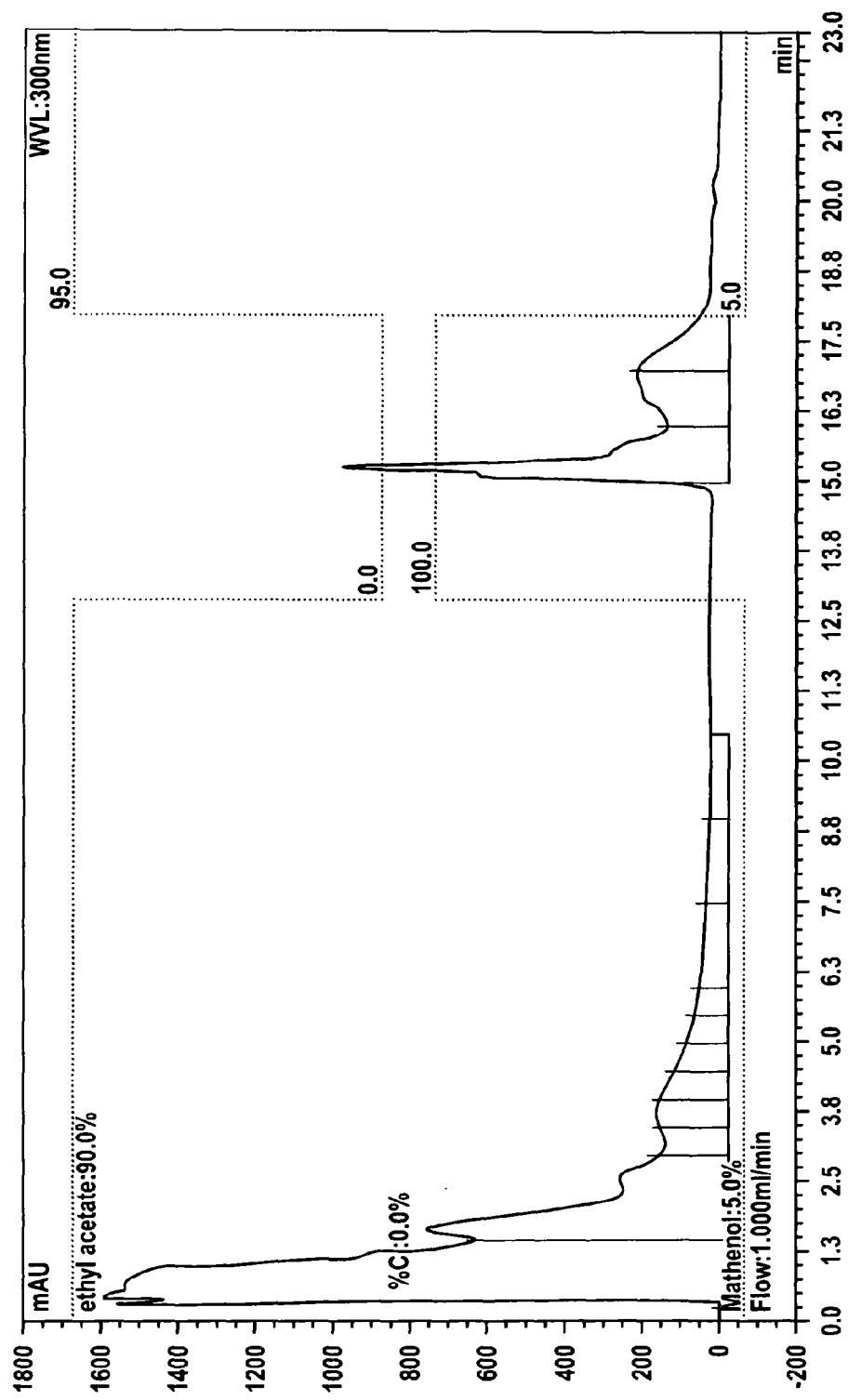

FIG. 4: Fractionation of paclitaxel according to Example 8.

Figure 5:
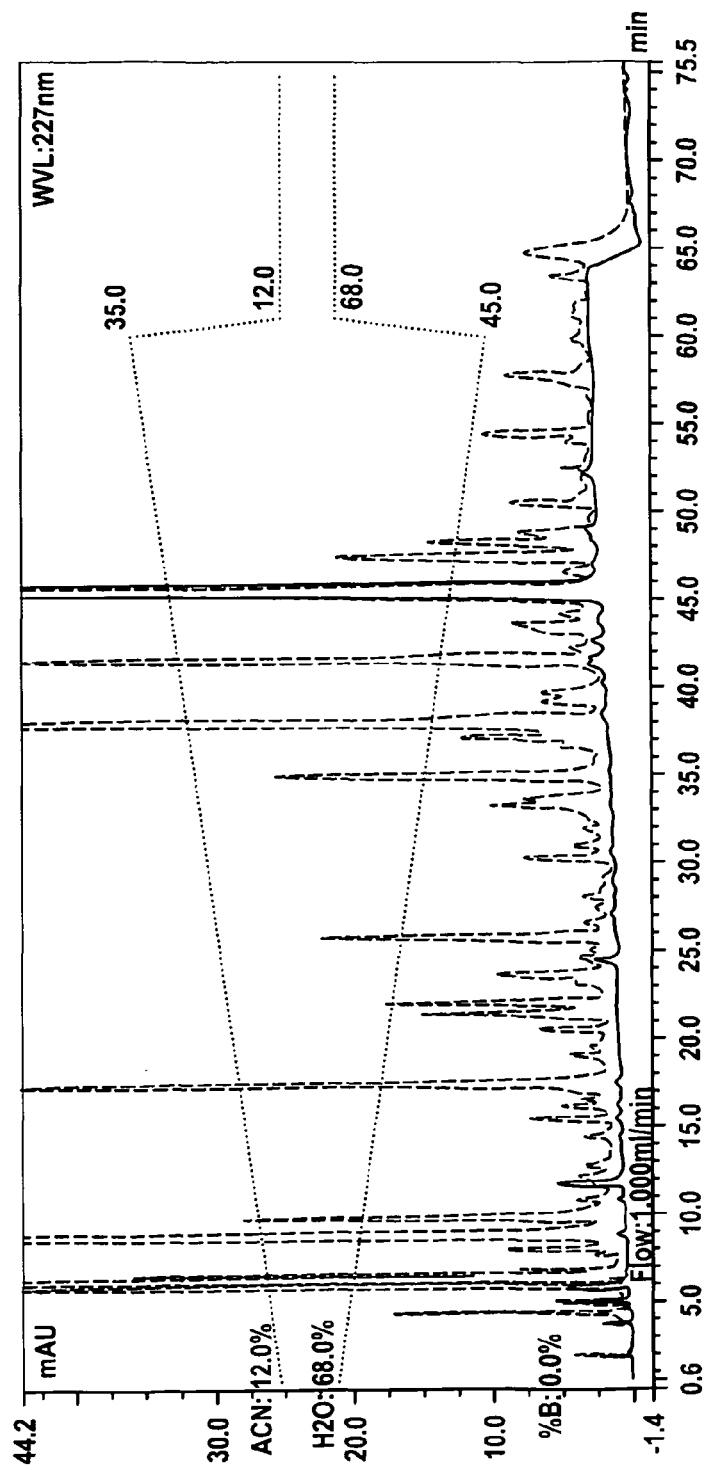

FIG. 5: Comparison of the analytical chromatograms of the crude paclitaxel (dashed line) and the purified paclitaxel (continuous line) (Example 8).

Figure 6:
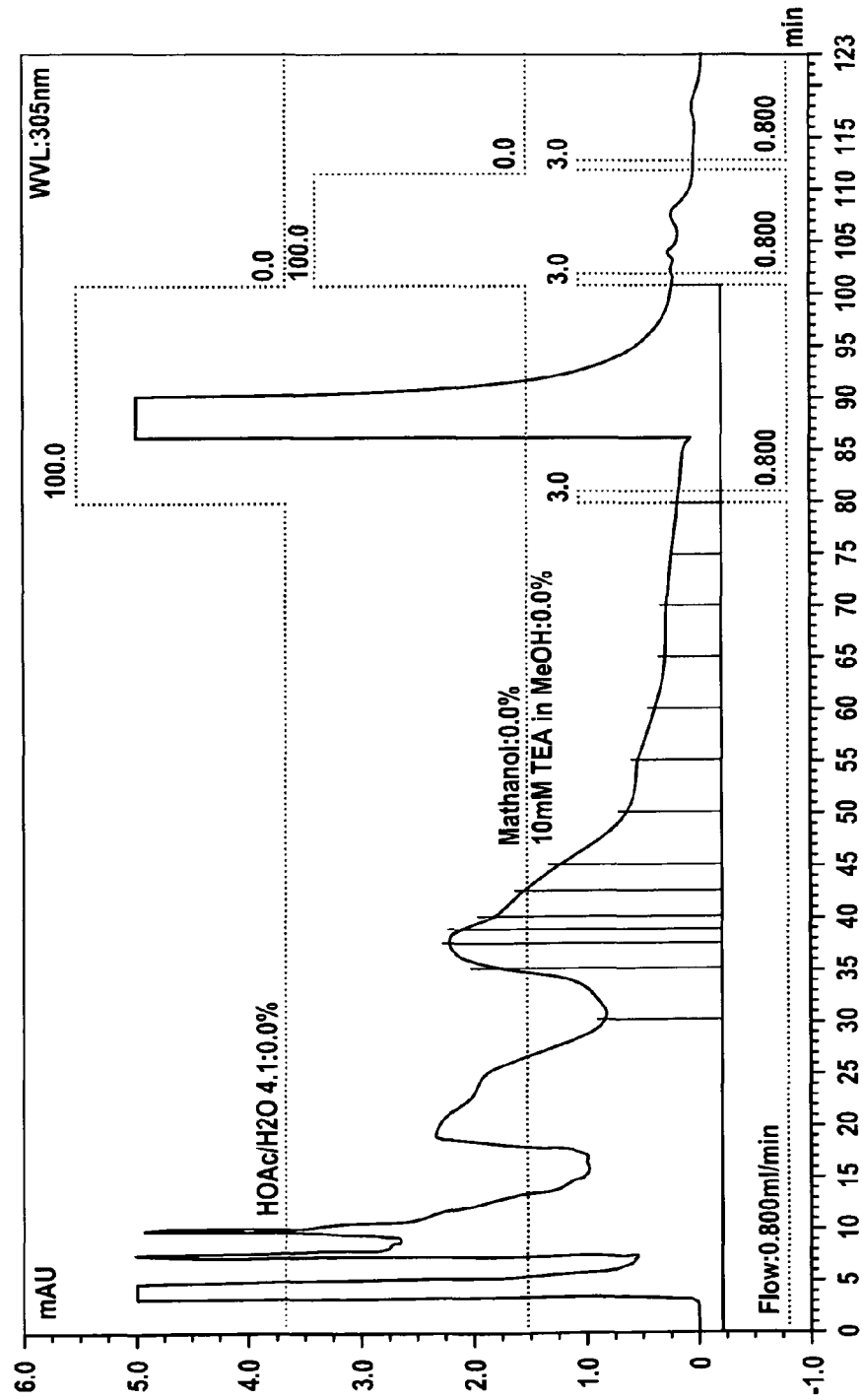

FIG. 6: Fractionation of 10-deacetyl-baccatin III according to Example 11.

Figure 7:
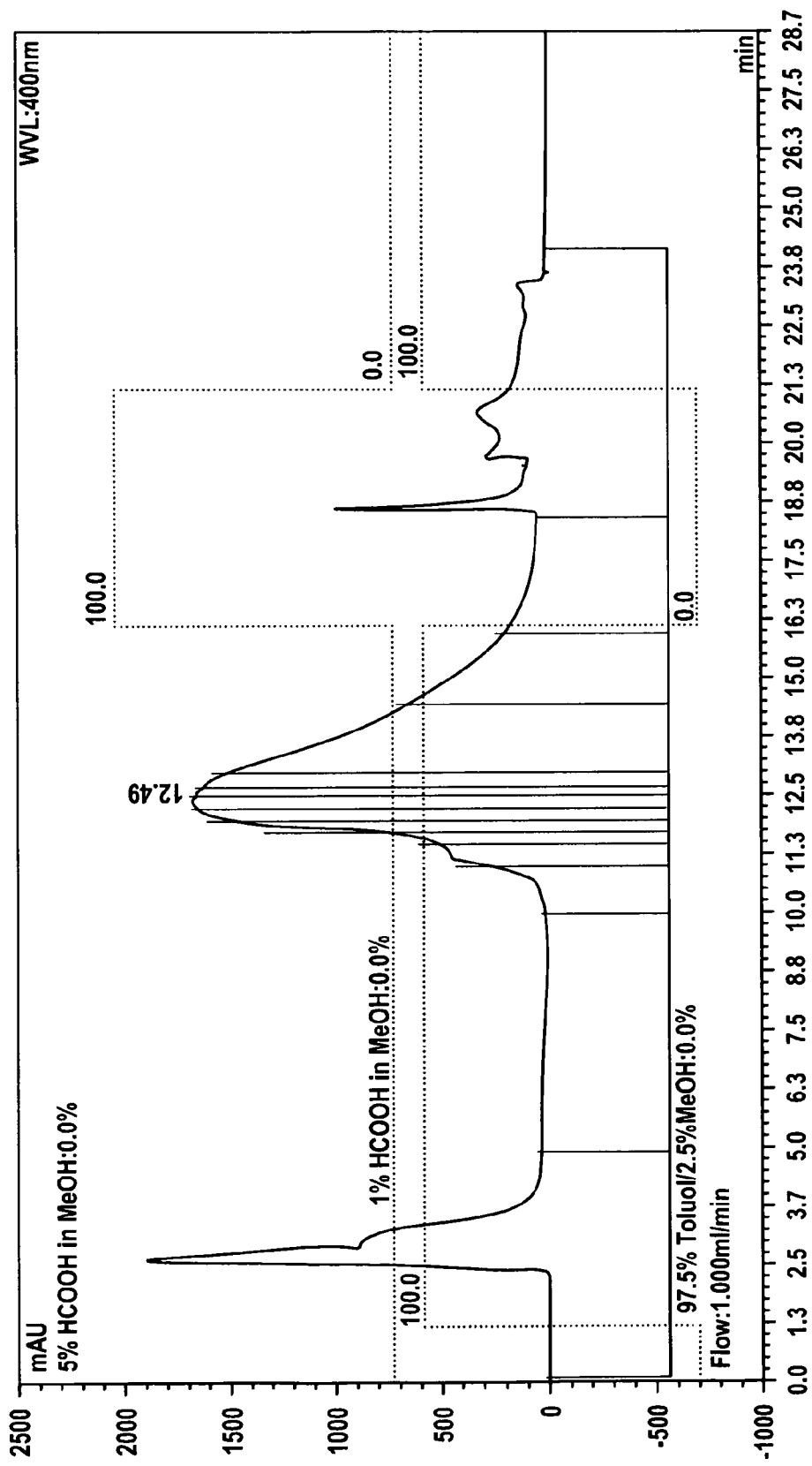

FIG. 7: Fractionation of montelukast according to Example 12.

Figure 8:
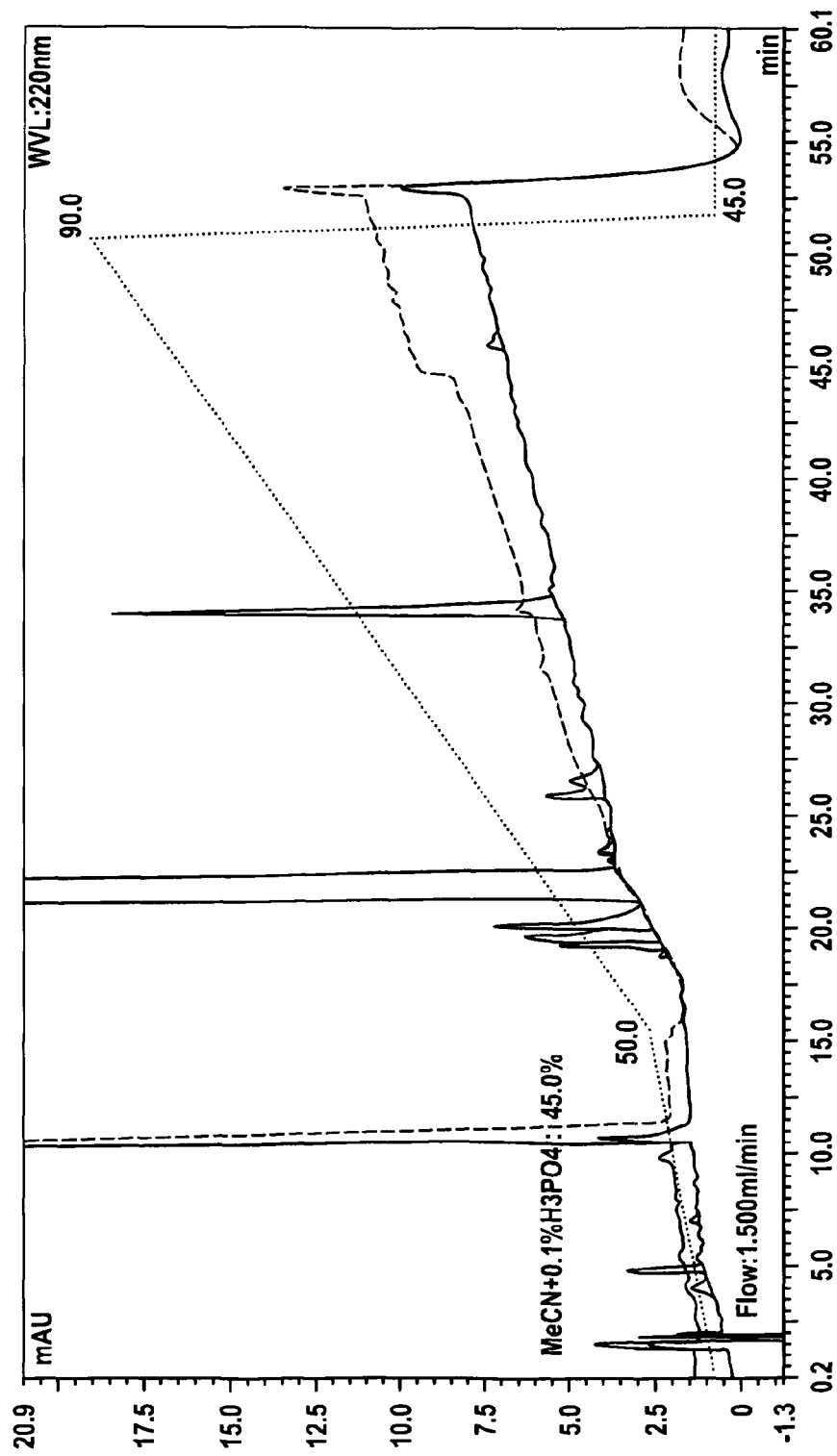

FIG. 8: Comparison of the analytical chromatograms of the crude montelukast (continuous line) and the purified product (dashed line) (Example 12).

Figure 9:
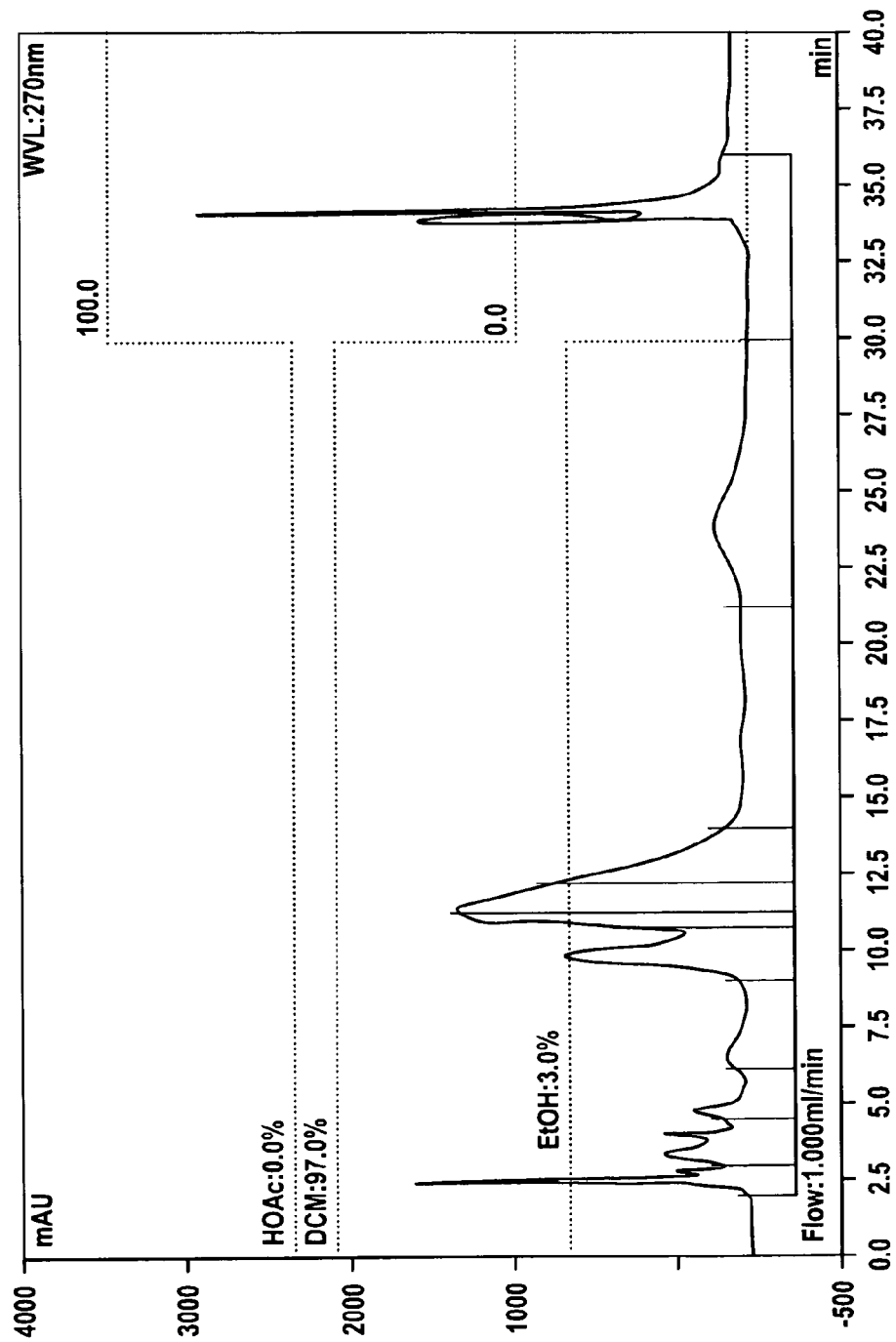

FIG. 9: Fractionation of docetaxel according to Example 13.

Figure 10:
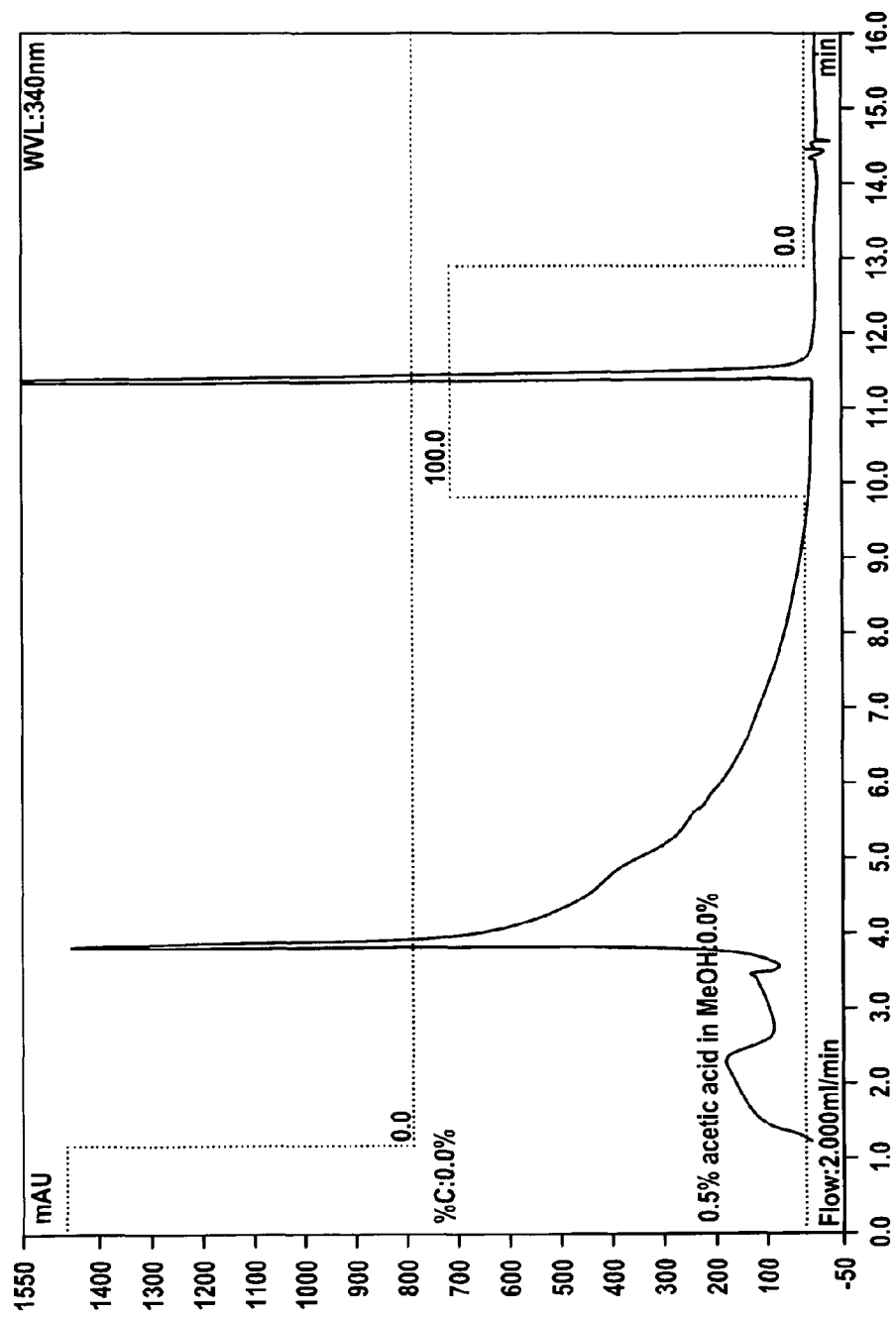

FIG. 10: Fractionation of fluocortolone according to Example 14. The product fraction can taken from to 5.5 to 11.5 min.

Figure 11:
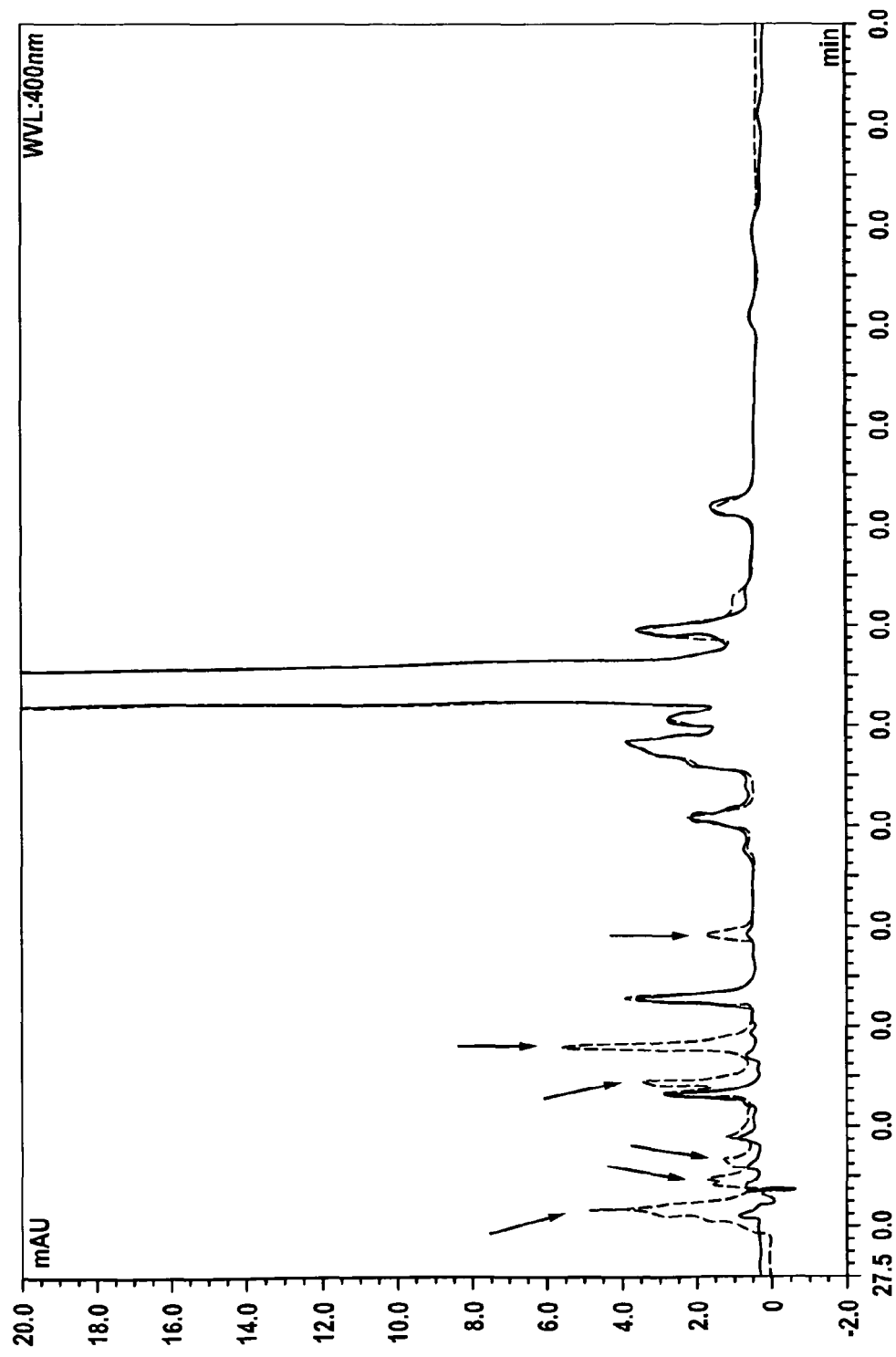

FIG. 11: Comparison of the analytical chromatograms of the crude fluocortolone (dashed line) and the purified product (continuous line), arrows indicate the main impurities (Example 14).

Figure 12:
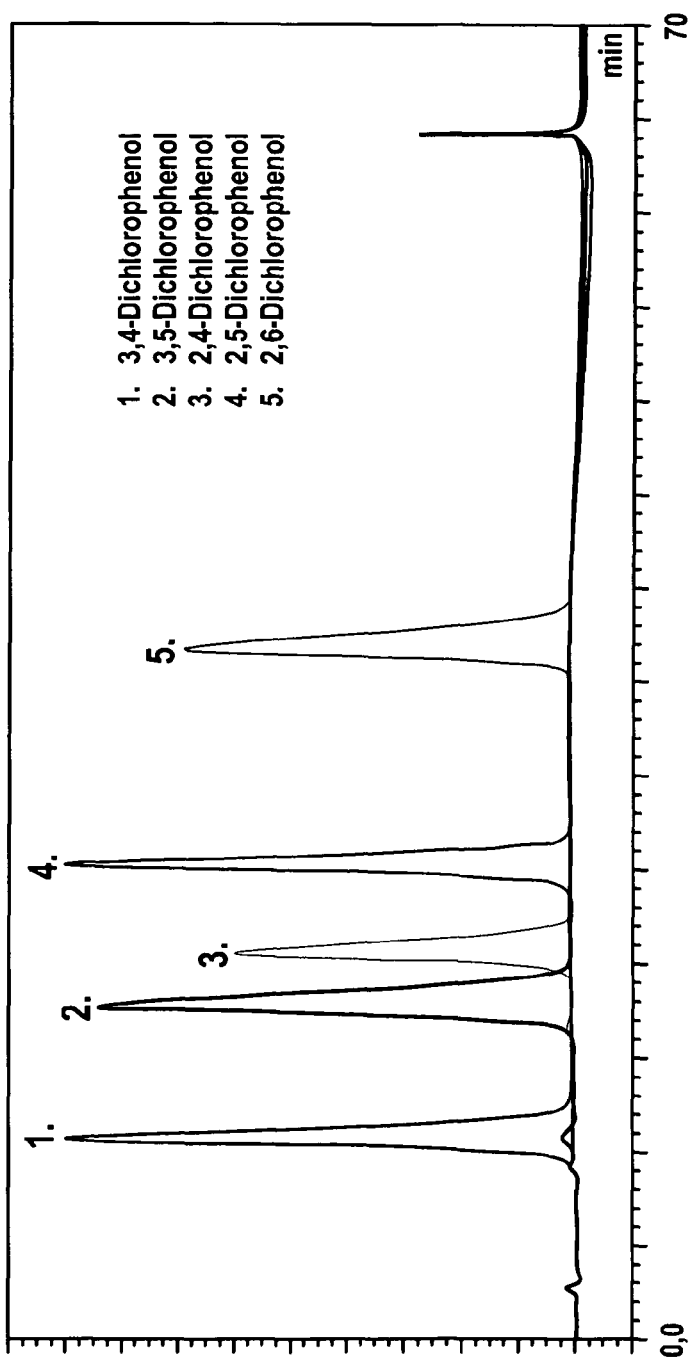

FIG. 12: Fractionation of different dichlorophenols according to Example 16 by using a sorbent according to the invention of Example 15.

Figure 13:
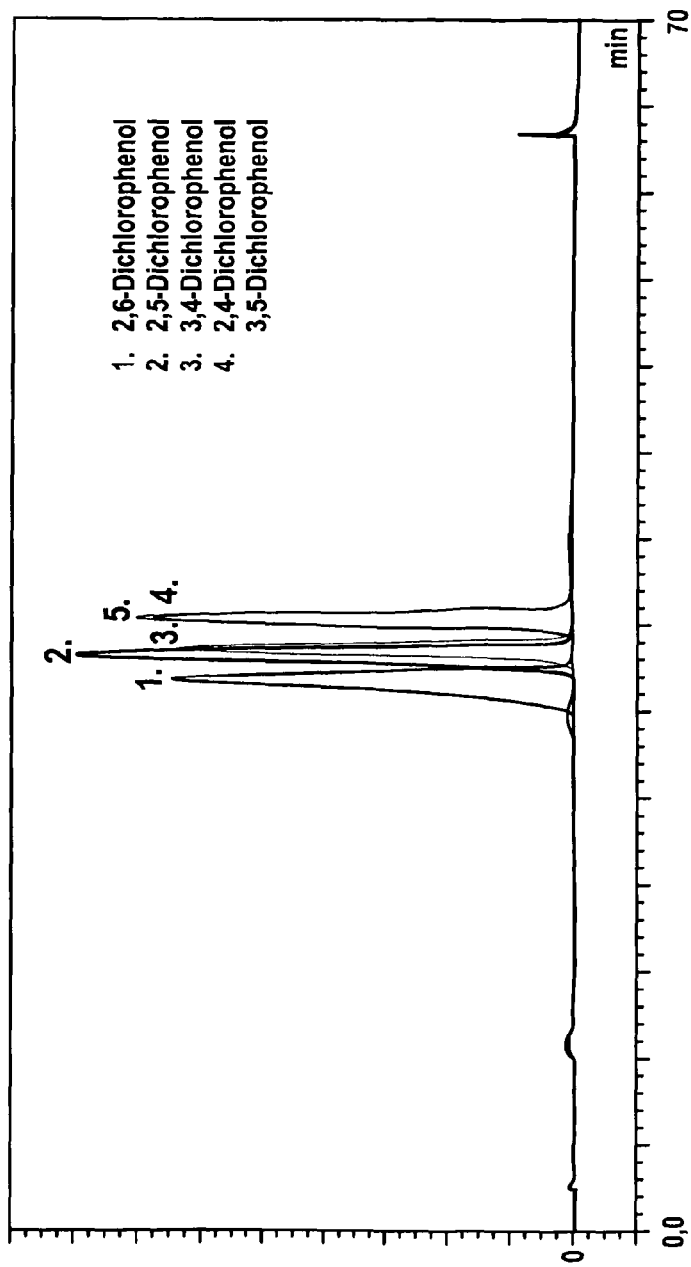

FIG. 13: Fractionation of different dichlorophenols according to Example 17 by using a commercially available Kromasil, C18, 100 Å, 10 μm sorbent.

Figure 14:
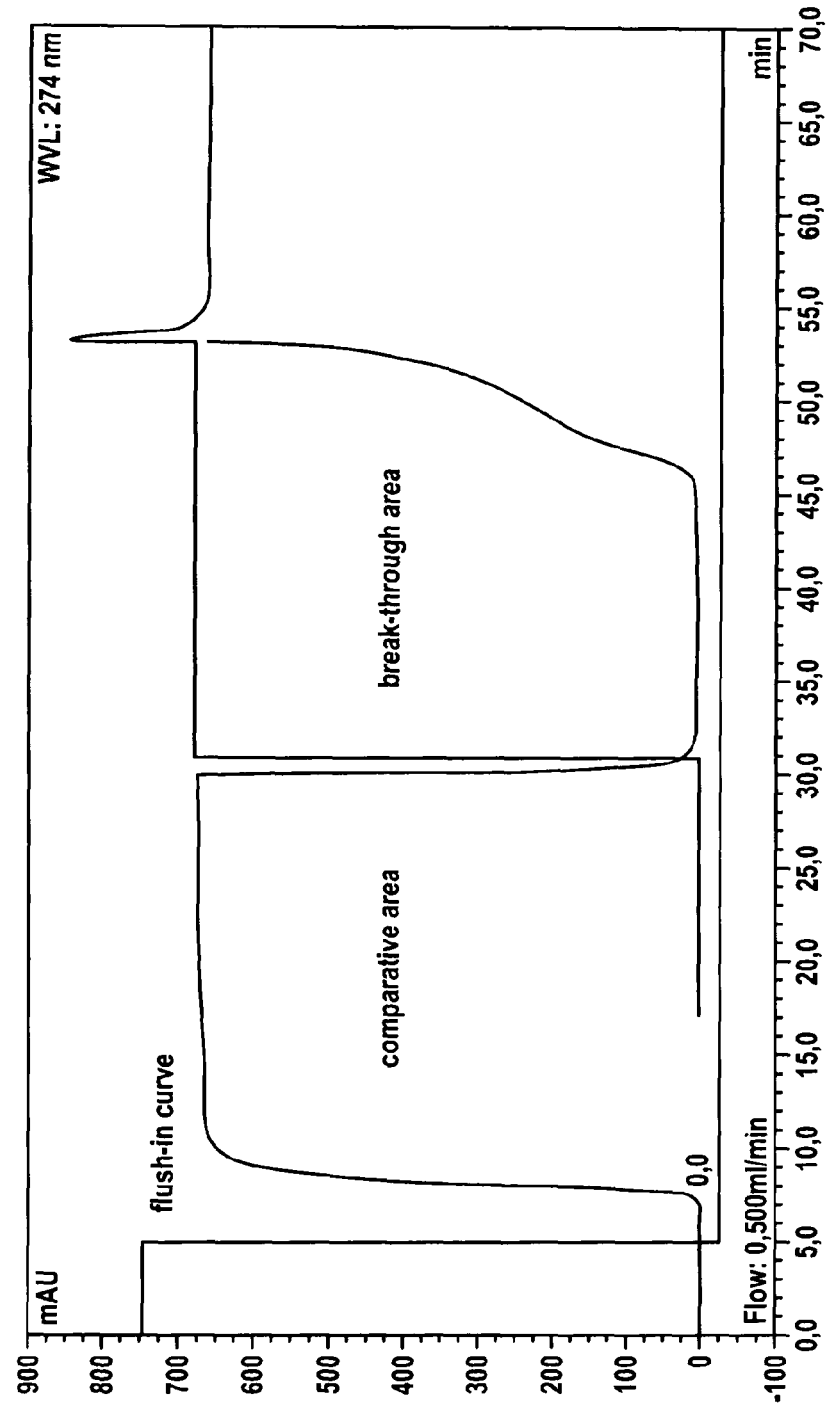

FIG. 14: Sample curve for the determination of the amount of amine groups by means of break-through measurement with 4-toluene sulfonic acid (front analysis).

Figure 15:
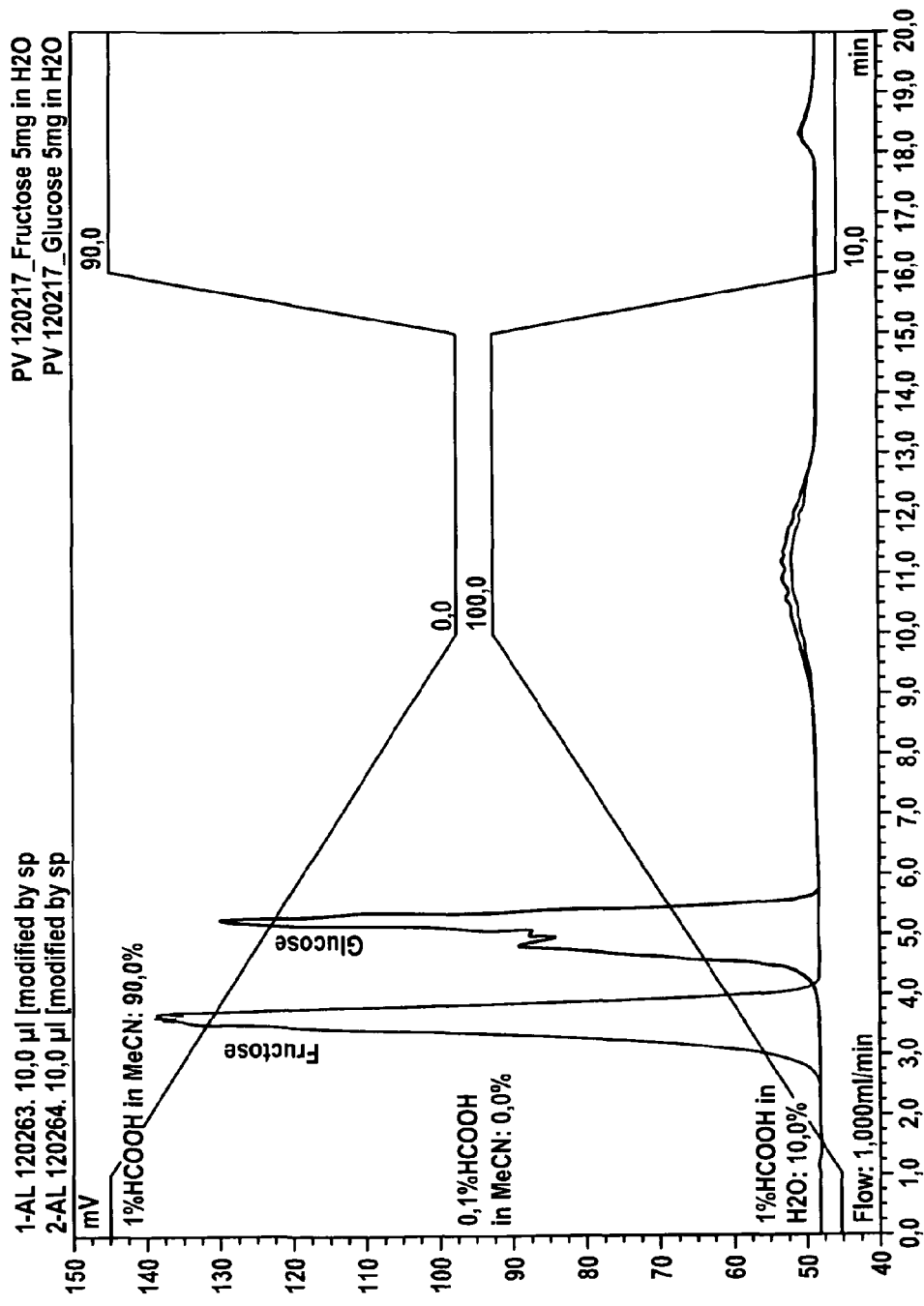

FIG. 15: Chromatogram of a sample fractionation of a crude mixture of sugars (see Example 18) separated by a sorbent according to the invention produced in Example 15.

Figure 16:
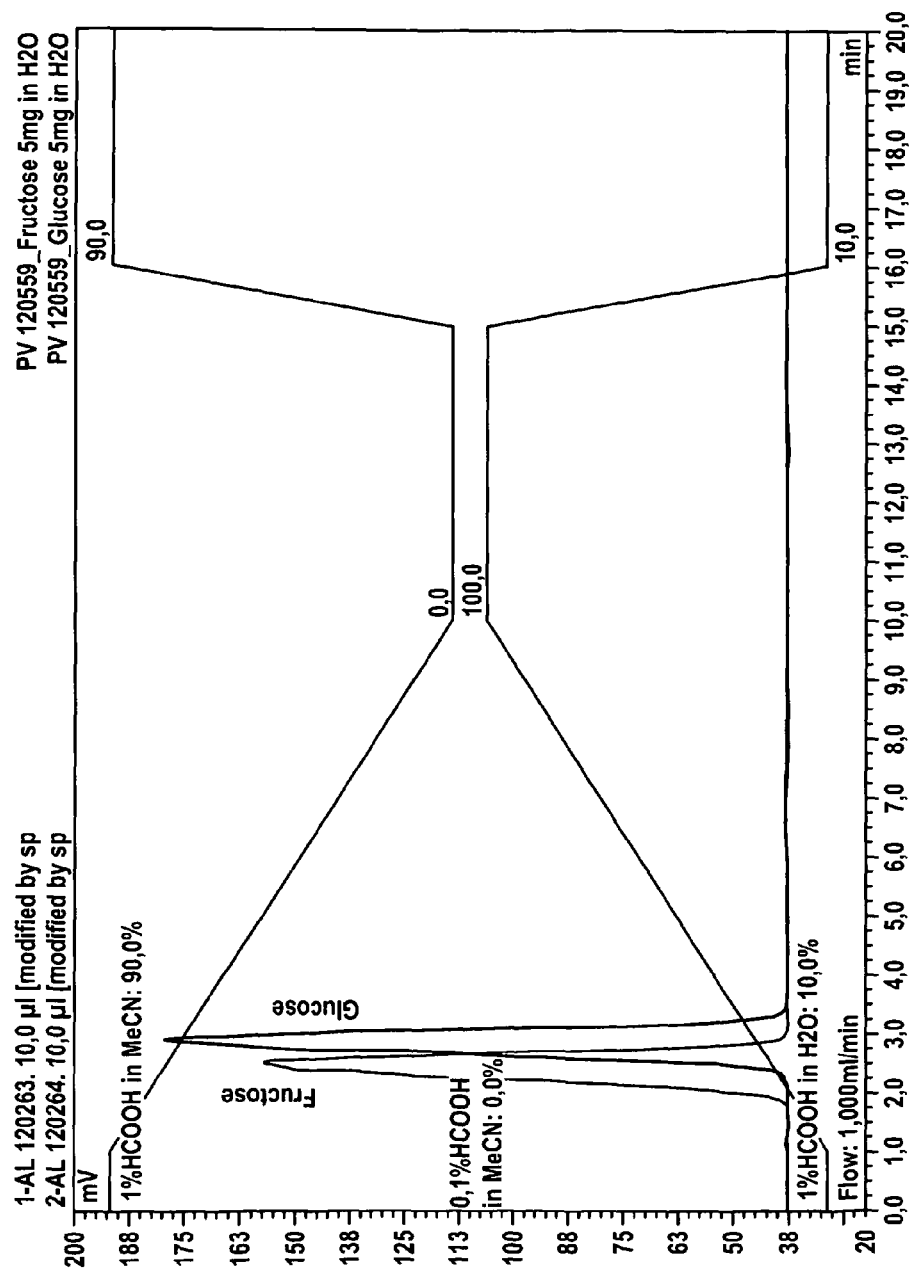

FIG. 16: Chromatogram of a sample fractionation of a crude mixture of sugars (see Example 19) separated by the commercially available sorbent Kromasil (NH$_2$, 100 Å, 10 μm)

EXAMPLES

Analytical Methods

Determination of the Amount of Amine Groups by Means of Break-Through Measurement with 4-Toluene Sulfonic Acid (Front Analysis)

The respective sorbent is packed to a column having the dimensions 33.5×4 mm (bed volume 0.42 mL). The filled column is then flushed with the following media at a flow rate of 1.0 mL/min:
5 mL of water
10 mL of a 100 mM aqueous solution of ammonium acetate
1 mL of water
10 mL of a 100 mM aqueous solution of trifluoroacetic acid
10 mL of water A base line is detected at a HPLC-device having a pump and a UV-detector after water has been pumped through the device for 5 min at 0.5 mL/min. After that a solution of 10 mM 4-toluene sulfonic acid in water is pumped through, whereas the extinction of the eluent is detected at 274 nm. The extinction rises in few minutes to a level of about 700 mAU and remains constant at this level (flush-in curve). After 25 min the column is applied between pump and detector and is flushed with 10 mM of 4-toluene sulfonic acid at 0.5 mL/min. The extinction then drops to 0 mAU since the column is binding 4-toluene sulfonic acid. If the capacity of the column is exhausted, the extinction of the eluate again rises to the starting level of ~700 mAU.

For the determination of the capacity of 4-toluene sulfonic acid the area below the level of the flush-in curve is integrated as comparative area, thereby obtaining the relationship between surface area and the amount of 4-toluene sulfonic acid. After that the area (break-through area) of the toluene sulfonic acid solution absorbed by the column is titrated, and the volume of the device and the dead volume of the column (0.5 mL) are subtracted. The break-through area directly indicates the amount of 4-toluene sulfonic acid bound to the column. Dividing this amount by the volume of the column yields in the capacity of toluene sulfonic acid per mL of the sorbent, also resulting in the amount of amine groups of the sorbent. For the better understanding of this method FIG. 14 shows such an example curve.

Example 1

Method of Producing a Sorbent According to the Invention Comprising a Residue of Formula (I)-1

Silicagel SP-1000-20 from DAISO was coated with polyvinyl amine using 2900 g of a 12.4% polyvinylamine solution in water with adjusted pH of 9.0 for 6000 g of silicagel. The mixture was agitated on a sieve shaker until the solution was fully soaked up in the pores of the silicagel. After that the sorbent was dried in vacuum at 50° C. until the water was completely evaporated. Afterwards the dried sorbent was suspended in 18 L isopropanol and agitated at 55° C. for 5 hours with 72.8 g of ethylene glycol diglycidyl ether. Afterwards the sorbent was filtered off and washed with 18 L isopropanol, 30 L 0.5 M trifluoroacetic acid in water, 30 L water and 30 L methanol. After drying the sorbent is ready for further modification.

The amount of amine groups of the resulting intermediate determinable by titration was about 442 µmol/mL.

13.5 L of the coated and crosslinked sorbent was washed with 20 L 0.5 M triethylenamine in dimethylformamide and afterwards suspended in 12.6 L DMF. 1991 g 2-(1H-Benzotriazole-1-yl)-1,1,3,3-tetramethyluronium hexafluorophosphate (HBTU) and 730 mL triethylene amine (TEA) were added and the mixture was agitated at 25° C. for 18 hours. After that the mixture was filtered off and the sorbent was washed with 5 L DMF, 20 L 0.5 M trifluoroacetic acid in DMF, 5 L DMF, 15 L 0.5 M TEA in DMF and 20 L DMF again. The sorbent was suspended in 9 L DMF and 996 g HBTU and 365 mL TEA were added. The mixture was again agitated for 18 hours at 25° C. After that the solution was filtered off and the sorbent washed with 5 L DMF, 20 L 0.5 M TFA in DMF, 30 L TFA in water, 30 L water and 30 L methanol. After drying at 50° C. in vacuum the sorbent is ready to use.

The resulting sorbent contains about 119 µmol/mL of the residues according to formula (I)-1, determined via elemental analysis. The ratio of the residues according to formula (I)-1 to the amounts of amine groups determined before derivatization is about 0.27.

Example 2

Method of Producing a Sorbent According to the Invention Comprising a Residue of Formula (I)-2

150 g of Daisogel SP-1000-10 from DAISO were coated with 133.9 g of an aqueous solution of 11.2% polyvinylamine as described in Example 1. The crosslinking was done in 560 mL DMF with 9.6 g 1,12-bis-(5-norbornen-2,3-dicarboximido)-decandicarboxylic acid at 25° C. for 4 hours. Afterwards the solution was filtered off and the sorbent washed with 1.8 L DMF, 3 L 0.5 M TFA in DMF, 6 L 0.1 M TFA in water, 1.8 L water and 1.8 L methanol. The sorbent was dried at 40° C. in vacuum.

10.5 g of the coated and crosslinked sorbent was washed with 300 mL 0.5 M triethylenamine in dimethylformamide and afterwards suspended in 20 mL water. 4.42 mL Glycidyltrimethylammoniumchloride solution (75% in water) was added and the mixture was agitated at 25° C. for 3 days. After that the mixture was filtered off and the sorbent was washed with 300 mL water, 300 mL 0.5 M TEA in DMF and 300 mL water. The sorbent was suspended in 20 mL water and 4.42 mL Glycidyltrimethylammoniumchloride solution (75% in water). The mixture was again agitated for 3 days at 25° C. After that the solution was filtered off and the sorbent washed with 300 mL water, 300 mL 0.1 M TFA in DMF, 500 mL TFA in water, 300 mL water and 300 mL methanol. After drying at 50° C. in vacuum the sorbent is ready to use.

Example 3

Method of Producing a Sorbent According to the Invention Comprising a Residue of Formula (I)-2 (Different Crosslinking)

The coating was performed with 145.2 g of a 12.4% solution of polyvinylamine in water for 300 g of silicagel. The crosslinking was done with 3.64 g ethyleneglycoldiglycidylether in 850 mL isopropanol for 4 hours at 25° C.

The amount of amine groups of the resulting intermediate determinable by titration was about 559 µmol/mL.

All other parameters and the modification of the coated sorbent was done according to Example 2.

The resulting sorbent contains about 268 μmol/mL of the residues according to formula (I)-2, determined via elemental analysis. The ratio of the residues according to formula (I)-2 to the amounts of amine groups determined before derivatization is about 0.48.

Example 4

Method of Producing a Sorbent According to the Invention Comprising a Residue of Formula (I)-3

25 g of Jupiter SP-300-15 from Phenomenex were coated with 20.4 g of an aqueous solution of 9.8% polyvinylamine as described in Example 1. The crosslinking was done in 150 mL dimethylformamide with 1.3 g, 1,12-bis-(5-norbornen-2,3-dicarboximido)-decandicarboxylic acid at 25° C. for 18 hours. Afterwards the solution was filtered off and the sorbent washed with 230 mL DMF, 780 mL 0.1 M TFA in watery 230 mL water and 230 mL methanol. The sorbent was dried at 40° C. in vacuum.

The amount of amine groups of the resulting intermediate determinable by titration was about 470 μmol/mL.

25 g of the coated silicagel was washed with 200 mL 0.5 mL TEA in DMF and afterwards suspended in 100 mL DMF. 4.43 g of 1-methylpiperazine-4-succinic acid amide, 8.4 g 2-(1H-Benzotriazole-1-yl)-1,1,3,3-tetramethyluronium hexafluoro-phosphate (HBTU) and 2.24 g triethylamine were added and the mixture was agitated for 12 hours at 25° C. The suspension was filtered off and the sorbent washed with 250 mL DMF, 400 mL 0.1 M TFA in DMF, 250 mL DMF and 300 mL 0.5 M TEA in DMF. The sorbent was suspended again in 100 mL DMF. 2.22 g of HBTU and 1.12 g triethylamine were added and the mixture was agitated for 12 hours at 25° C. The suspension was filtered off and the sorbent washed with 250 mL DMF, 400 mL 0.1 M TFA in water, 250 mL water and 250 mL methanol. After drying at 50° C. in vacuum the sorbent was ready for use.

The resulting sorbent contains about 410 μmol/mL of the residues according to formula (I)-3, determined via elemental analysis. The ratio of the residues according to formula (I)-3 to the amounts of amine groups determined before derivatization is about 0.87.

Example 5

Method of Producing a Sorbent According to the Invention Comprising a Residue of Formula (I)-3 (Different Solid Support)

Silicagel SP-100-10 from DAISO was coated with polyvinylamine using 59.7 g of a 13.4% polyvinylamine solution in water and additional 40 g of water with adjusted pH of 9.5 for 100 g of silicagel. The mixture was agitated on a sieve shaker until the solution was fully soaked up in the pores of the silicagel. After that the sorbent was dried in vacuum at 50° C. until the water was completely evaporated. Afterwards the dried sorbent was suspended in 300 mL isopropanol and agitated at 55° C. for 5 hours with 1.62 g of ethylene glycol diglycidyl ether. Afterwards the sorbent was filtered off and washed with 500 mL isopropanol, 500 mL 0.5 M trifluoroacetic acid in water, 500 L water and 500 L methanol. After drying the sorbent is ready for further modification.

The amount of amine groups of the resulting intermediate determinable by titration was about 596 μmol/mL.

The modification was done according to Example 4, adjusting the amounts to the amount of sorbent used for the modification.

The resulting sorbent contains about 423 μmol/mL of the residues according to formula (I)-3, determined via elemental analysis. The ratio of the residues according to formula (I)-3 to the amounts of amine groups determined before derivatization is about 0.71.

Example 6

Method of Producing a Sorbent According to the Invention Comprising Residues of Formula (I)-1 and Residues of Formula (I)-2

1200 g Silicagel SP-1000-10 from DAISO was coated with polyvinylamine using 600 g of a 12.0% polyvinylamine solution in water with additional 340 g water. The pH was adjusted to 9.3 and the mixture was agitated on a sieve shaker until the solution was fully soaked up in the pores of the silicagel. After that the sorbent was dried in vacuum at 50° C. until the water was completely evaporated. Afterwards the dried sorbent was suspended in 4.4 L isopropanol and agitated at 50° C. for 4 hours with 14.5 g of ethylene glycol diglycidyl ether. Afterwards the sorbent was filtered off and washed with 7 L isopropanol, 14 L 0.5 M trifluoroacetic acid in water, 14 L water and 8 L methanol. After drying the sorbent is ready for further modification.

The amount of amine groups of the resulting intermediate determinable by titration about 494 μmol/mL.

For the first modification the sorbent was washed with 13 L 0.5 TEA in DMF and afterwards suspended in 2 L DMF. 465 g HBTU and 171 mL TEA were added and the mixture was stirred for 19 hours at 25° C. and afterwards filtered off and washed with 1.5 L DMF, 1.5 L 0.5 TEA in DMF, 1.5 L DMF, 1.5 L 0.5 M TEA in DMF and 1.15 L DMF. The mixture was suspended again in 2 L DMF. 465 g HBTU and 171 mL TEA were added and the mixture was stirred another 19 hours at 25° C. Afterwards it was filtered off and washed with 1.5 L DMF, 1.5 L 0.5 TFA in DMF, 1.5 L DMF, 1.5 L 0.5 M TEA in DMF and 1.5 L DMF.

The second modification was done according to Example 2 in two steps with 183.2 glycidytrimethylammoniumchloride and 122.2 g TEA in 3.5 L DMF for 1.3 kg of coated sorbent.

The resulting sorbent contains about 114 μmol/mL of the residues according to formula (I)-1, and 5 μmol/mL of the residues according to formula (I)-2 determined via elemental analysis. The ratio of the residues according to formulae (I)-1 and (I)-2 to the amounts of amine groups determined before derivatization is about 0.24.

Example 7

Purification of Pentamycin by Using the Sorbent Produced in Example 1

The crude mixture of pentamycin and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 1 was filled in a 250×50.8 mm steel column. The method for separation is shown in Table 1.

TABLE 1

Method for the purification of pentamycin:

| Time [min] | Stabilized THF [%] | Methanol [%] | Water/Glacial Acetic Acid 2/8 [%] | Flow Rate [mL/min] |
|---|---|---|---|---|
| 0 | 92 | 8 | | 239 |
| 40 | 92 | 8 | | 239 |
| 40 | | | 100 | 318 |
| 45 | | | 100 | 318 |
| 45 | 92 | 8 | | 318 |
| 58 | 92 | 8 | | 318 |
| 58 | 92 | 8 | | 318 |
| 60 | 92 | 8 | | 239 |

The analytics of several fractionations is shown in the Table 2 below.

TABLE 2

Analytical results of several fractionations (EW1 to EW4) of a crude mixture of pentamycin:

| Fraction Collection [min:sec] | Compound | EW1 [%] | EW2 [%] | EW3 [%] | EW4 [%] | Average [%] |
|---|---|---|---|---|---|---|
| 24:30 to 40:00 | RRT 0.58 | 0.10 | 0.10 | 0.09 | 0.11 | 0.10 |
| | RRT 0.90 | 0.80 | 0.80 | 0.83 | 0.79 | 0.81 |
| | Pentamycin | 97.64 | 97.58 | 97.63 | 97.62 | 97.62 |
| | RRT 1.46 | 0.73 | 0.72 | 0.73 | 0.72 | 0.73 |

*RRT: relative retention time in the analytical chromatogram

FIG. 1 shows the reduction of the main impurities from chromatogram 1 (crude; continuous line) to chromatogram 2 (purified; dashed line).

Sorbents similarly produced according ms Example 1 comprising less than 100 µmol/mL of residues according to formula (I)-1 (ligand) lead to lower purities and yields than the sorbent of Example 1. Lowering the amount of ligand to less than 80 µmol/mL decreases the purification capacity and yield significantly. If the amount of ligand is lowered to less than 50 µmol/mL almost no selectivity for pentamycin is observed.

In the same way, sorbents having a molar ratio of the residues according to formula (I)-1 to the amount of functional groups of the polymer of less than 0.2 are more than 20% deteriorated with respect to the purity and yield of the obtainable pentamycin, since the retention is very low.

Example 8

Purification of Paclitaxel by Using the Sorbent Produced in Example 2

The crude mixture of paclitaxel and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 2 was filled in a 40×4 mm steel column. Paclitaxel was purified in a single chromatographic step using an isocratic method of 5% methanol in acetyl acetate. The course of the fractionation is shown in FIG. 4. The different fractions (B1 to B4) taken are shown in Table 3.

TABLE 3

Purity and yield of paclitaxel in the different fractions taken:

| Fraction No. | Purity [%] | Yield [%] |
|---|---|---|
| B1 | 0.59 | 2.2 |
| B2 | 0.66 | 0.4 |
| B3 | 3.53 | 0.4 |
| B4 | 26.71 | 3.0 |
| B5 | 90.29 | 20.3 |
| B6 | 96.79 | 26.4 |
| B7 | 96.71 | 21.5 |
| B8 | 96.65 | 11.9 |
| B9 | 83.5 | 12.3 |
| B10 | 24.52 | 1.1 |
| B11 | 14.09 | 0.2 |
| B12 | 0.57 | 0.3 |
| B13 | 3.55 | 0.1 |
| B14 | 3.73 | 0.0 |

The depletion of the impurities could be well seen in FIG. 5 in which the crude mixture (dashed chromatogram) is compared to the purified product (continuous line).

Example 9

Purification of Sugammadex by Using the Sorbent Produced in Example 3

The crude mixture of sugammadex and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 3 was filled in a axial compressed ModCol 250× 25.4 mm steel column. Sugammadex was purified using an isocratic method with 60% methanol in (total) 500 mM aqueous formic acid. FIG. 3 shows the chromatogram of the fractionation with the different fractions taken. The content of the different fractions is shown in Table 4.

TABLE 4

Content of the different fractions (AS1 to AS6) of the main product Org_25_AT (sugammadex) and different impurities Org_48_C, Org_19_B etc.:

| | Purity Org_25_AT [%] | Purity Org_48_C [%] | Purity Org_19_B [%] | Purity Peak RRT 2.4 [%] | Yield Org_25_AT [%] |
|---|---|---|---|---|---|
| Fractions | | | | | |
| AS1 | 1.72 | 13.44 | 16.1 | 3.38 | 0 |
| AS2 | 7.34 | 74.4 | 11.75 | 1.7 | 0 |

TABLE 4-continued

Content of the different fractions (AS1 to AS6) of
the main product Org__25__AT (sugammadex) and different
impurities Org__48__C, Org__19__B etc.:

|  | Purity Org__25__AT [%] | Purity Org__48__C [%] | Purity Org__19__B [%] | Purity Peak RRT 2.4 [%] | Yield Org__25__AT [%] |
|---|---|---|---|---|---|
| AS3 | 96.11 | 2.32 | 0.89 | 0.23 | 12 |
| AS4 | 98.54 | 0.69 | 0.32 | 0.15 | 28 |
| AS5 | 98.97 | 0.18 | 0.08 | 0.17 | 59 |
| AS6 | 10.03 | 0 | 0 | 3.1 | 0 |
| Virtual Combined Fractions | | | | | |
| AS3-AS5 | 98.50 | 0.59 | 0.25 | 0.17 | 99 |
| AS4-AS5 | 98.83 | 0.35 | 0.16 | 0.16 | 87 |
| starting quality of batch Z | 92.86 | 4.68 | 1.12 | 0.16 | |

RRT: relative retention time in the analytical chromatogram

Sorbents similarly produced according to Example 3 comprising more than 100 μmol/mL of residues according to formula (I)-2 (ligand) still showed an acceptable purification capacity in good yields. Lowering the amount of ligand to less than 80 μmol/mL decreases the purification capacity and yield significantly. If the amount of ligand is lowered to less than 50 μmol/mL no selectivity for sugammadex is observed.

In the same way, sorbents having a molar ratio of the residues according to formula (I)-2 to the amount of functional groups of the polymer of more than 0.2 still showed a selectivity for sugammadex. Sorbents wherein the ratio is less than 0.2 showed only very low or almost no selectivity for sugammadex.

Example 10

Purification of Paclitaxel by Using the Sorbent Produced in Example 4

The crude mixture of paclitaxel and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching calves (Besta), column oven and a diode-array uv detector (UVD 170U, UVD 340S or VWD 3400). The sorbent produced in Example 4 was filled in a 33.5×4 mm steel column. Paclitaxel was purified in a single chromatographic step using an isocratic method of hexane/ethyl acetate/methanol 50/44/6 with a starting purity of 93% to a purity of 99.34% in 68% yield and 99.22% purity in 92% yield respectively. The course of the fractionation is shown in FIG. 2. The critical impurities 7-epipaclitaxel, 2-debenzoyl-2-tigloylpaclitaxel, 2'-O-benzoylpaclitaxel and 7,13-bis-sidechain-paclitaxel are depleted below 0.1%, and in some cases close to or even below the limit of the uv detection as shown in Table 5.

TABLE 5

Content of the different fractions (J1 to J10) taken during fractionation:

|  | Paclitaxel | | 7-epi-Paclitaxel | | 2-Debenzoyl-2-tigloyl-Paclitaxel | |
|---|---|---|---|---|---|---|
| fraction | Purity [%] | Yield [%] | Purity [%] | Yield [%] | Purity [%] | Yield [%] |
| J 1 | 0.16 | 0.00 | 6.936 | 82.38 | 0.051 | 0.57 |
| J 2 | 92.474 | 4.29 | 0.583 | 15.15 | 2.987 | 69.26 |
| J 3 | 98.889 | 13.33 | 0.016 | 1.24 | 0.133 | 8.99 |
| J 4 | 99.419 | 12.42 | 0.003 | 0.22 | 0.078 | 4.89 |
| J 5 | 99.361 | 19.86 | 0.006 | 0.73 | 0.045 | 4.56 |
| J 6 | 99.338 | 15.80 | 0.003 | 0.29 | 0.015 | 1.22 |
| J 7 | 99.288 | 20.13 | | | 0.028 | 2.87 |
| J 8 | 98.804 | 10.37 | | | 0.083 | 4.33 |
| J 9 | 96.87 | 3.07 | | | 0.209 | 3.31 |
| J 10 | 10.88 | 0.73 | | | | 0.00 |

Sorbents similarly produced according to Example 4 comprising more than 200 μmol/mL of residues according to formula (I)-3 (ligand) still showed purification capacities of more than 80% of that of the sorbent according to Example 4. By lowering the amount of ligand to about 80 μmol/mL the purification capacity and yield was still in an acceptable range. If the amount of ligand is lowered to less than 50 μmol/mL no selectivity for paclitaxel is observed anymore.

In the same way, sorbents having a molar ratio of the residues according to formula (I)-3 to the amount of functional groups of the polymer of more than 0.2 still resulted in a high purity of paclitaxel, even if in very low yield. Sorbents wherein the ratio is less than 0.2 showed only very low or almost no selectivity for paclitaxel.

Example 11

Purification of 10-D-Acetyl-Baccatin III by Using the Sorbent Produced in Example 4

The crude mixture of 10-D-acetyl-baccatin III and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 4 was filled in a 250×20 mm steel column. 10-D-acetyl-baccatin III was purified according to the method shown in Table 6. The fractionation of 10-deacetyl-baccatin III is shown in FIG. 5.

TABLE 6

Chromatographic method for the purification of 10-D-acetyl-baccatin III:

| time [min] | flow rate [mL/min] | hexane | ethyl-acetate | methanol | acetic acid/water 4:1 |
|---|---|---|---|---|---|
| 0 | 20 | 59 | 34 | 7 | 0 |
| 80 | 20 | 59 | 34 | 7 | 0 |
| 80.1 | 20 | 0 | 0 | 0 | 100 |
| 100 | 20 | 0 | 0 | 0 | 100 |
| 100.1 | 20 | 0 | 0 | 100 | 0 |
| 110 | 20 | 0 | 0 | 100 | 0 |
| 110.1 | 20 | 59 | 34 | 7 | 0 |
| 120 | 20 | 59 | 34 | 7 | 0 |

The fractions taken were analyzed according to Table 7.

TABLE 7

Analytic results of the different fractions (AG1 to AG15) taken:

| fraction | purity [%] | yield [%] |
|---|---|---|
| AG1 | 0 | 0 |
| AG2 | 0 | 0 |
| AG3 | 0 | 0 |
| AG4 | 35.94 | 1 |
| AG5 | 71.06 | 3 |
| AG6 | 83.03 | 9 |
| AG7 | 86.79 | 9 |
| AG8 | 90.49 | 19 |
| AG9 | 93.67 | 19 |
| AG10 | 89.33 | 16 |
| AG11 | 84.99 | 11 |
| AG12 | 83.53 | 7 |
| AG13 | 79.3 | 3 |
| AG14 | 73.38 | 4 |
| AG15 | 0 | 0 |

Sorbents similarly produced according to Example 3 comprising more than 100 μmol/mL of residues according to formula (I)-3 (ligand) still showed an acceptable purification capacity in good yields. Lowering the amount of ligand to less than 80 μmol/mL decreases the purification capacity and yield significantly. If the amount of ligand is lowered to less than 50 μmol/mL no selectivity for 10-D-acetyl-baccatin III is observed.

In the same way, sorbents having a molar ratio of the residues according to formula (I)-3 to the amount of functional groups of the polymer of more than 0.2 still showed a selectivity for 10-D-acetyl-baccatin III. Sorbents wherein the ratio is less than 0.2 showed only very low or almost no selectivity for 10-D-acetyl-baccatin III.

Example 12

Purification of Montelukast by Using the Sorbent Produced in Example 5

The crude mixture of montelukast and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 5 was filled in a 250×4 mm steel column. For purification an isocratic method with toluene/methanol 97.5/2.5 was used. FIG. 7 shows the course of the fractionation. Montelukast could be obtained in 99.8% purity with 82% yield starting from 95.0% purity in the crude mixture. FIG. 8 shows the analytical chromatogram of the purified product (dashed line) in comparison to the crude mixture (continuous line).

Sorbents similarly produced according to Example 5 comprising more than 100 μmol/mL of residues according to formula (I)-3 (ligand) still showed an acceptable purification capacity in good yields. Lowering the amount of ligand to less than 80 μmol/mL decreases the purification capacity and yield significantly. If the amount of ligand is lowered to less than 50 μmol/mL no selectivity for montelukast is observed.

In the same way, sorbents having a molar ratio of the residues according to formula (I)-3 to the amount of functional groups of the polymer of more than 0.2 still showed a selectivity for montelukast. Sorbents wherein the ratio is less than 0.2 showed only very low or almost no selectivity for montelukast.

Example 13

Purification of Docetaxel by Using the Sorbent Produced in Example 4

The crude mixture of docetaxel and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 4 was filled in a 250×4 mm steel column. For purification an isocratic method with dichloromethane/ethyl acetate 97/3 was used. FIG. 9 shows the course of the fractionation. Docetaxel could be obtained in 99.03% purity with 84% yield.

Sorbents similarly produced according to Example 4 comprising more than 200 μmol/mL of residues according to formula (I)-3 (ligand) still showed purification capacities of more than 80% of that of the sorbent according to Example 4. By lowering the amount of ligand to about 80 μmol/mL the purification capacity and yield was still in an acceptable range. If the amount of ligand is lowered to less than 50 μmol/mL no selectivity for docetaxel is observed anymore.

In the same way, sorbents having a molar ratio of the residues according to formula (I)-3 to the amount of functional groups of the polymer of more than 0.2 still resulted in a high purity of docetaxel, even if in low yield. Sorbents wherein the ratio is less than 0.2 showed only very low or almost no selectivity for docetaxel.

Example 14

Purification of Fluocortolone by Using the Sorbent Produced in Example 6

The crude mixture of fluocortolone and several impurities were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 6 was filled in a 40×4 nm steel column. For purification an isocratic method of 100% dichloromethane and 1% acetic acid in methanol for the washing step was used. FIG. 10 shows the course of the fractionation and FIG. 11 the analytical chromatograms of the crude (dashed line) and the purified product continuous line).

Fluocortolone could be obtained in 99.0% purity and 93% yield with this method.

Sorbents similarly produced according to Example 6 comprising less than 100 µmol/mL of residues according to formulae (I)-1 and (I)-2 (ligand) lead to lower purities and yields than the sorbent of Example 6. Lowering the amount of ligand to less than 80 µmol/mL decreases the purification capacity and yield significantly. If the amount of ligand is lowered to less than 50 µmol/mL almost no selectivity for fluocortolone is observed.

In the same way, sorbents having a molar ratio of the residues according to formulae (I)-1 and (I)-2 to the amount of functional groups of the polymer of less than 0.2 are more than 10% deteriorated with respect to the purity and yield of the obtainable fluocortolone.

Example 15

Method of Producing a Sorbent According to the Invention Comprising a Residue of Formula (I)-4

Silicagel SP-120-10 from DAISO was coated with polyvinylamine using 254 g of a 11.8% polyvinylamine solution in water with adjusted pH between 8.0 and 8.5 and diluted with additional 250 g of water for 600 g of silicagel. The mixture was agitated on a sieve shaker until the solution was fully soaked up in the pores of the silicagel. After that the sorbent was dried in vacuum at 50° C. until the water was completely evaporated. Afterwards the dried sorbent was suspended in 2700 mL isopropanol and agitated at 55° C. for 5 hours with 12.12 g of Ethylene glycol diglycidyl ether. Afterwards the sorbent was filtered off and washed with 3000 mL isopropanol, 9000 mL 0.1 M hydrochloric acid (HCl) in water, 3000 mL water and 4500 mL methanol. After drying the sorbent is ready for further modification.

The amount of amine groups of the resulting intermediate determinable by titration was about 720 µmol/mL.

50 g of the coated and crosslinked sorbent was suspended in 150 mL DMF, 300 washed with 300 mL DMF, 300 mL 0.5 M triethylamine (TEA) in DMF, 300 mL DMF and suspended in 150 mL DMF again. 5.76 g L-Carnitine, 13.56 g O-Benzotriazol-1-yl-tetramethyluroniumhexafluorophosphate and 4.98 g TEA were added and the mixture was agitated at 50° C. for 4 hours. After that the mixture was filtered off and the resin was treated for a second reaction step as above. After that, the resin was washed with 300 mL DMF, 300 mL 0.1 M HCl in DMF, 300 mL 0.1 M HCl in water, 300 mL water and 300 mL methanol. After drying at 50° C. in vacuum the sorbent is ready to use.

The resulting sorbent contains about 612 µmol/mL of the residues according to formula (I)-4, determined via elemental analysis. The ratio of the residues according to formula (I)-4 to the amounts of amine groups determined before derivatization is about 0.85.

Example 16

Separation of Different Dichlorophenols by Using the Sorbent Produced in Example 15

A crude mixture of comprising 3,4-dichlorophenol, 3,5-dichlorophenol, 2,4-dichlorophenol, 2,5-dichlorophenol and 2,6-dichlorophenol were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 15 was filled in a 250×4 mm steel column. For purification different gradients of two eluents (A and B) were used as can be seen from Table 8 below. Eluent A is water and eluent B is acetonitril.

FIG. 12 shows the course of the fractionation.

TABLE 8

| | gradient 1 | | |
|---|---|---|---|
| time [min] | flow rate [mL/min] | Eluent A $H_2O$ [%] | Eluent B MeCN [%] |
| 0 | 1.00 | 0 | 100 |
| 1 | 1.00 | 0 | 100 |
| 10 | 1.00 | 100 | 0 |
| 15 | 1.00 | 100 | 0 |
| 15 | 1.00 | 0 | 100 |
| 20 | 1.00 | 0 | 100 |

Sorbents similarly produced according to Example 15 comprising more than 100 µmol/mL of residues according to formula (I)-4 (ligand) still showed an acceptable separation. Lowering the amount of ligand to less than 80 µmol/mL decreases the separation capacity. If the amount of ligand is lowered to less than 50 µmol/mL no separation is observed.

In the same way, sorbents having a molar ratio of the residues according to formula (I)-4 to the amount of functional groups of the polymer of 0.2 or more still separated in sufficient manner. Sorbents wherein the ratio is less than 0.2 showed only very low separation.

Example 17 (Comparative)

Separation of Different Dichlorophenols by Using the Sorbent Kromasil (C18, 100 Å, 10 µm)

Exactly the same separation method as in Example 16 is applied apart from using the sorbent Kromasil (C18, 100 Å, 10 µm). The course of fractionation is shown in FIG. 13.

Example 18

Separation of a Mixture of Glucose and Fructose by Using the Sorbent Produced in Example 15

A crude mixture of comprising glucose and fructose were separated using an Dionex HPLC system consisting of a four channel low-pressure gradient pump (LPG 580, LPG 680 or LPG 3400), auto sampler (Gina 50, ASI-100 or WPS-300), six-channel column switching valves (Besta), column oven and a diode-array uv detector (UVD 170U, UVD 340S or VWD 3400). The sorbent produced in Example 15 was filled in a 40×4 mm steel column. For purification different gradients of two eluents (A and B) were used as can be seen from Table 9 below. Eluent A is water containing 1 wt.-% formic acid and eluent B is acetonitril containing 1 wt.-% formic acid.

FIG. 15 shows the course of fractionation.

TABLE 9

| | | | gradient 1 | |
|---|---|---|---|---|
| time [min] | Flow rate [mL/min] | Eluent A H$_2$O 1% HCOOH [%] | Eluent B MeCN 1% HCOOH [%] | |
| 0 | 1.00 | 10 | 90 | |
| 1 | 1.00 | 10 | 90 | |
| 10 | 1.00 | 100 | 0 | |
| 15 | 1.00 | 100 | 0 | |
| 15 | 1.00 | 10 | 90 | |
| 20 | 1.00 | 10 | 90 | |

Sorbents similarly produced according to Example 15 comprising more than 100 μmol/mL of residues according to formula (I)-4 (ligand) still showed an acceptable separation. Lowering the amount of ligand to less than 80 μmol/ml decreases the separation capacity. If the amount of ligand is lowered to less than 50 μmol/mL no separation is observed.

In the same way, sorbents having a molar ratio of the residues according to formula (I)-4 to the amount of functional groups of the polymer of 0.2 or more still separated in sufficient manner. Sorbents wherein the ratio is less than 0.2 showed only very low separation.

Example 19 (Comparative)

Separation of a Mixture of Sugars by Using the Sorbent Kromasil (NH$_2$, 100 Å, 10 μm)

Exactly the same separation method as in Example 18 is applied apart from using the sorbent Kromasil (C18, 100 Å, 10 μm). The course of fractionation is shown in FIG. 16.

The invention claimed is:

1. A sorbent comprising a solid support material, wherein the surface of the solid support material comprises a residue of the following general formula (I):

formula (I)

wherein the residue is attached via a covalent single bond represented by the dotted line in formula (I) to a functional group on the surface of either the bulk solid support material itself or a polymer film on the surface of the solid support material, and wherein:
(a) L represents a covalent single bond or is an (h+1)-valent linear aliphatic hydrocarbon group comprising 1 to 30 carbon atoms, or an (h+1)-valent branched or cyclic aliphatic hydrocarbon group comprising 3 to 30 carbon atoms, wherein:
 (i) one or more CH$_2$-moieties in said groups may be substituted by a —C(O)—, —C(O)NH—, O, S, or —S(O)$_2$—; and
 (ii) one or more hydrogen atoms may be substituted by D, F, Cl, or OH;
(b) P$_B$ represents n organic cationic group or an organic protonizable group;
(c) h is an index representing the number of P$_B$-moieties bound to L and is 1, 2 or 3; and
with the proviso that, if L represents a covalent single bond, h is 1 and P$_B$ binds to the functional group via a carbon atom of the group P$_B$.

2. The sorbent of claim 1, wherein P$_B$ is a group comprising at least one nitrogen atom in the form of an amine.

3. The sorbent of claim 2, wherein the amine is a primary, secondary, tertiary or quaternary amine.

4. The sorbent of claim 3, wherein P$_B$ is a group selected from one of the following groups (a) to (e):

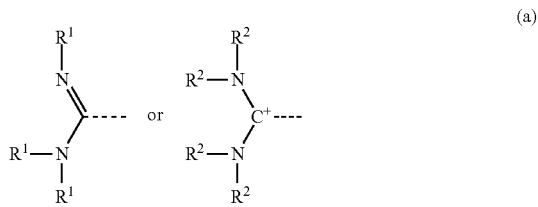

(a)

wherein R$^1$ is independently at each occurrence H or C$_{1-6}$-alkyl, and
R$^2$ is independently at each occurrence a C$_{1-6}$-alkyl;

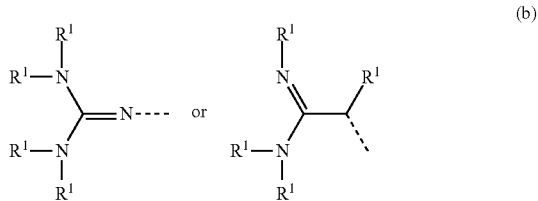

(b)

wherein R$^1$ is independently at each occurrence H or C$_{1-6}$-alkyl, and
wherein each R$^1$ of the group N(R$^1$)$_2$ may form together with each R$^1$ of the other groups, independently of each other, a unit —(CH$_2$)p-, wherein p is 2, 3, 4 or 5;
(c) —N(R$^3$)$_2$ or —[N(R$^3$)$_3$], wherein R$^3$ is H, C$_{1-6}$-alkyl, a mono or polycyclic aromatic ring system or a mono- or polycyclic heteroaromatic ring system;
(d) pyrrolidine, piperidine, morpholine or piperazine, being substituted in position 4 with R$^3$ as defined in (c); and
(e) —NH—(C$_{1-6}$-alkylene)-NH$_2$.

5. The sorbent of claim 4, wherein P$_B$ is one of the following groups:

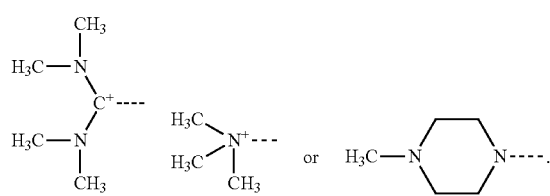

6. The sorbent of claim 1, wherein L is selected from the group consisting of
a covalent single bond,
—(C$_{1-6}$-alkylene)-,
—(C$_{1-6}$-alkylene)-CH(OH)—(C$_{1-6}$-alkylene),
—(C$_{1-6}$-alkylene)-X—(C$_{1-6}$-alkylene)-, wherein X is O, S or —S(O)$_2$—,
—(C$_{1-3}$-alkylene)-CH(OH)—(C$_{1-3}$-alkylene)-O—(C$_{1-6}$-alkylene)-O—(C$_{1-3}$-alkylene)-CH(OH)—(C$_{1-3}$-alkylene)-,
—C(O)—, —C(O)—(C$_{1-6}$-alkylene)-,
—C(O)—(C$_{1-3}$-alkylene)-CH(OH)—(C$_{1-3}$-alkylene)-,
—C(O)—CH(NHC(O)O—(C$_{1-6}$-alkyl))-(C$_{1-6}$-alkylene)-,
—C(O)—(C$_{1-6}$-alkylene)-C(O)—,
—C(O)—(C$_{1-6}$-alkylene)-C(O)—NH—,
—C(O)—(C$_{1-6}$-alkylene)-C(O)—NH—(C$_{1-6}$-alkylene)-,
—C(O)—(C$_{1-6}$-alkylene)-NH—C(O)—(C$_{1-6}$-alkylene)-,
and

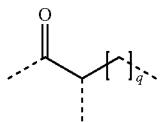

wherein q is 1, 2, 3, 4, 5, 6, 7 or 8; and
wherein the dotted lines or free ending lines represent the bonds to the functional group of either the solid support material or the polymer film and P$_B$.

7. The sorbent of claim 1, wherein h is 1.

8. The sorbent of claim 1, wherein the residue of formula (I) is one of the following:

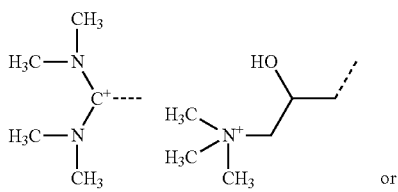

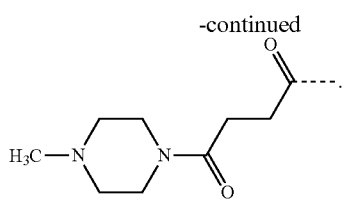

9. The sorbent of claim 1, wherein the sorbent comprises two or more different residues of formula (I).

10. The sorbent of claim 1, wherein the surface of the solid support material is covered with a polymer film comprising individual chains which are covalently cross-linked with each other, and wherein the individual chains are not covalently bound to the surface of the solid support material.

11. The sorbent of claim 10, wherein the polymer is a polyamine, a polyvinylamine, a copolymer comprising polyamine or a polymer blend comprising polyamine.

12. A method for the purification of organic molecules, comprising contacting organic molecules with the sorbent of claim 1.

13. The method of claim 12, wherein the organic molecules comprise one or more anionic or deprotonizable groups and/or a plurality of hydroxyl or chloro groups.

14. The method of claim 12, wherein the organic molecules exhibit a molecular weight in a range of from 100 to 200000 g/mol.

15. The method of claim 12, wherein the organic molecules are selected from the group consisting of paclitaxel, 10-D-acetyl-baccatin III, montelukast, docetaxel, sugmmadex, pentamycine, fluocortolone, derivatives thereof and endotoxines.

* * * * *